United States Patent
Snyder et al.

(10) Patent No.: US 7,358,237 B2
(45) Date of Patent: Apr. 15, 2008

(54) INDUCIBLE NITRIC OXIDE SYNTHASE BINDS, S-NITROSYLATES, AND ACTIVATES CYCLOOXYGENASE-2

(75) Inventors: Solomon H. Snyder, Baltimore, MD (US); Sangwon Kim, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 11/413,201

(22) Filed: Apr. 28, 2006

(65) Prior Publication Data

US 2006/0246076 A1 Nov. 2, 2006

Related U.S. Application Data

(60) Provisional application No. 60/675,552, filed on Apr. 28, 2005.

(51) Int. Cl.
*A61K 38/10* (2006.01)
*A61K 38/16* (2006.01)

(52) U.S. Cl. ............................ 514/200; 514/12; 514/13

(58) Field of Classification Search ...................... None
See application file for complete search history.

(56) References Cited

U.S. PATENT DOCUMENTS

| 5,543,297 A | 8/1996 | Cromlish et al. |
| 2003/0082550 A1 | 5/2003 | Thomann et al. |

OTHER PUBLICATIONS

Wiendl H et al., Therapeutic approaches in multiple sclerosis, 2002, Biodrugs, 16(3) p. 183-200.*
European Search Report and Written Opinion of PCT/US06/6294.
D. Salvemini et al., "Nitric Oxide Activates Cyclooxygenase Enzymes," *Proc. Natl. Acad. Sci. USA*, Aug. 1993, pp. 7240-7244, vol. 90.
S. F. Kim et al., "Inducible Nitric Oxide Synthase Binds, S-Nitrosylates, and Activates Cyclooxygenase-2," *Science*, Dec. 23, 2005, pp. 1966-1970, vol. 310.
T. Hla et al., "Human Cyclooxygenase-2 cDNA," *Proc. Nail. Acad. Sci. USA*, Aug. 1992, pp. 7384-7388, vol. 89.
GenPept AAA58433. Reports Cyclooxygenase-2 . . . [gi:181254](NCBI).
J. M. Braughler et al., "Effects of Thiols, Sugars, and Proteins on Nitric Oxide Activation of Guanylate Cyclase," *The Journal of Biological Chemistry*, Dec. 25, 1979, pp. 12450-12454, vol. 254, No. 24.
T. A. Kennedy et al., "Investigation of the Role of Cysteines in Catalysis by Prostaglandin Endoperoxide Synthase," *The Journal of Biological Chemistry*, Nov. 4, 1994, pp. 27357-27364, vol. 269, No. 44.
Y. Yang et al., "S-Nitrosoprotein Formation and Localization in Endothelial Cells," *Proc. Natl. Acad. Sci., USA*, Jan. 4, 2005, pp. 117-122, vol. 102, No. 1.
Lawrence J. Marnett et al., "Regulation of Prostaglandin Biosynthesis by Nitric Oxide is Revealed by Targeted Deletion of Inducible Nitric-Oxide Synthase," *The Journal of Biological Chemistry*, May 5, 2000, pp. 13427-13430, vol. 275, No. 18.
R. L. Patterson et al., "Inositol 1,4,5-Trisphosphate Receptor/GAPDH Complex Augments $Ca^{2+}$ Release Via Locally Derived NADH," *Proc. Natl. Acad. Sci., USA*, Feb. 1, 2005, pp. 1357-1359, vol. 102, No. 5.
H. Guhring et al., "Suppressed Injury-Induced Rise in Spinal Prostaglandin $E_2$ Production and Reduced Early Thermal Hyperalgesia in iNOS-Deficient Mice," *The Journal of Neuroscience*, Sep. 1, 2000 20(18):6714-6720.

* cited by examiner

*Primary Examiner*—Anish Gupta
*Assistant Examiner*—Ronald T Niebauer
(74) *Attorney, Agent, or Firm*—Banner & Witcoff, Ltd.

(57) ABSTRACT

Cyclooxygenase (COX2) and inducible nitric oxide synthase (iNOS) are two major inflammatory mediators. Inducible NOS specifically binds to COX2 and S-nitrosylates it, enhancing COX2 catalytic activity. Selectively disrupting iNOS—COX2 binding prevents NO-mediated activation of COX2. The synergistic molecular interaction between two inflammatory systems permits assays for developing anti-inflammatory drugs.

2 Claims, 10 Drawing Sheets

FIG. 2.
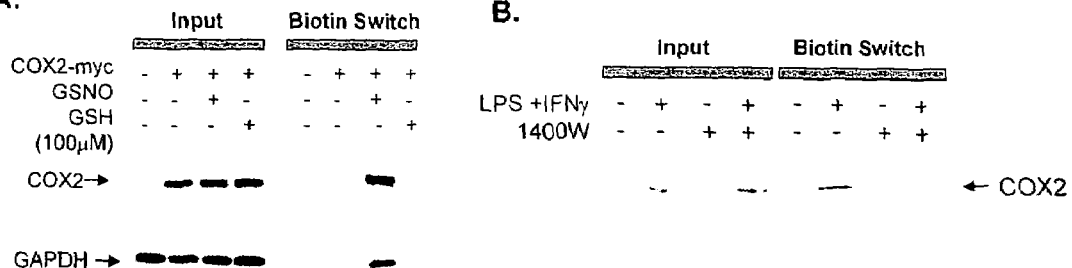
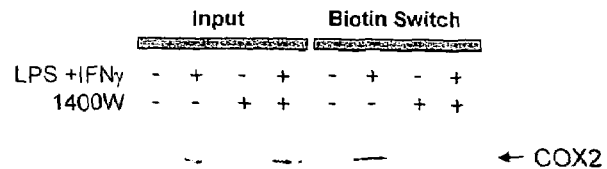
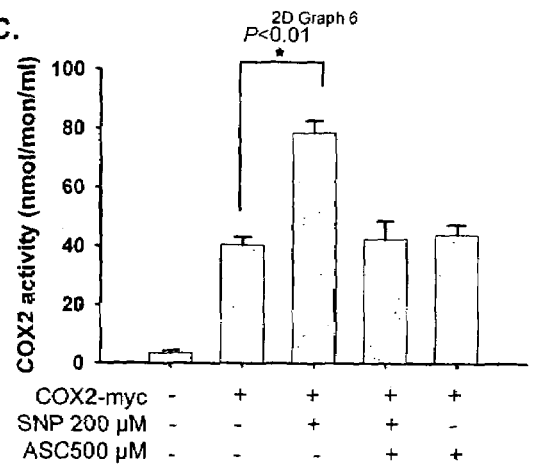
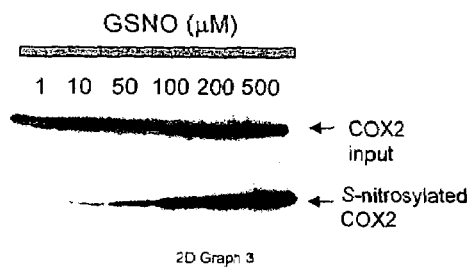
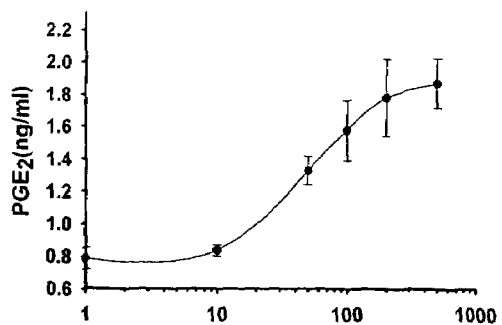
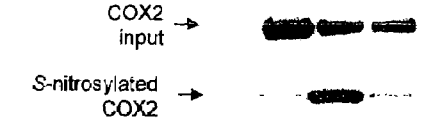
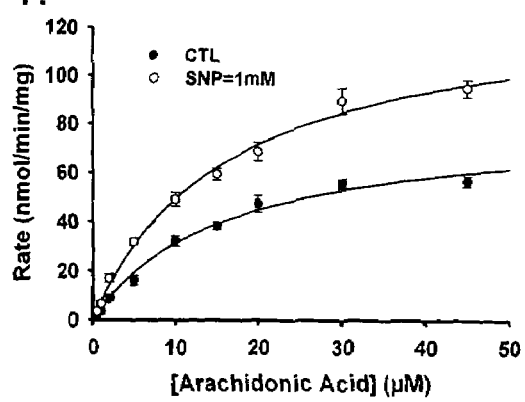
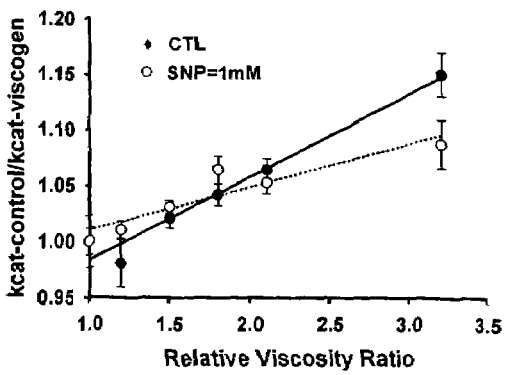

FIG. 3.
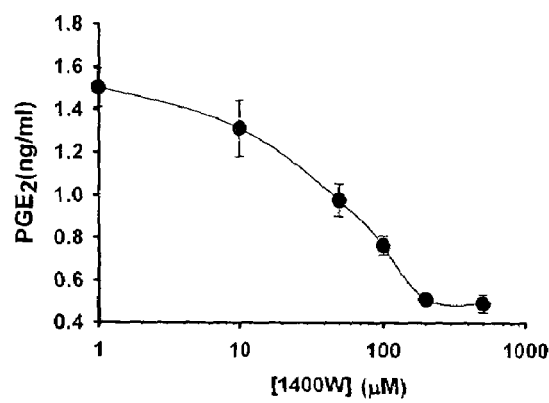
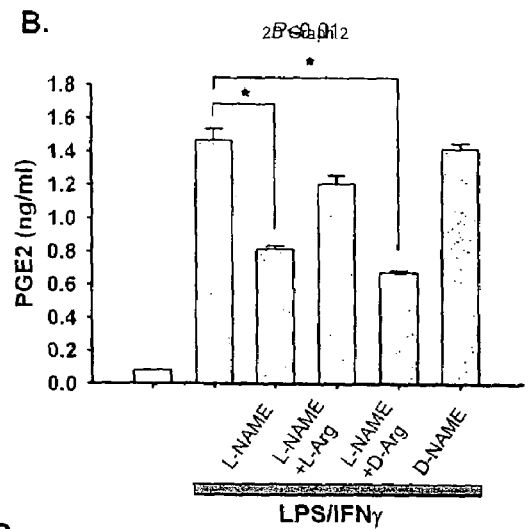
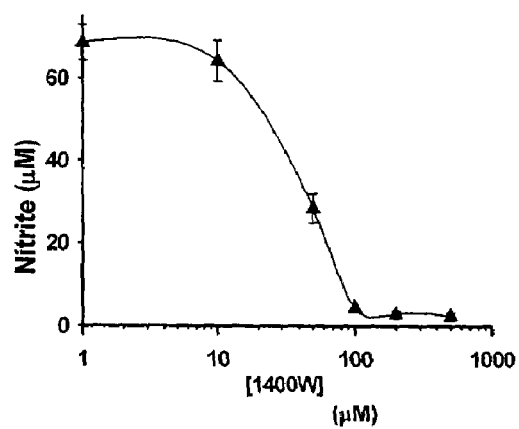
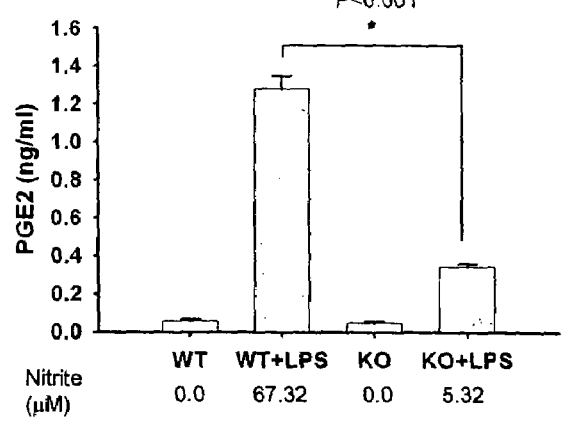
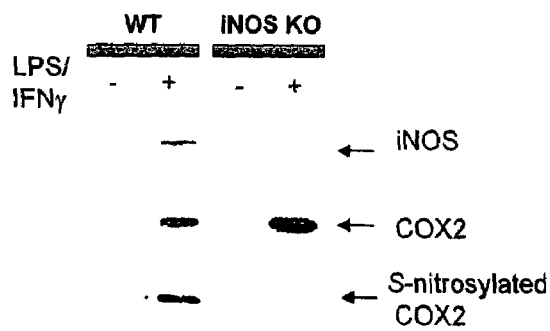

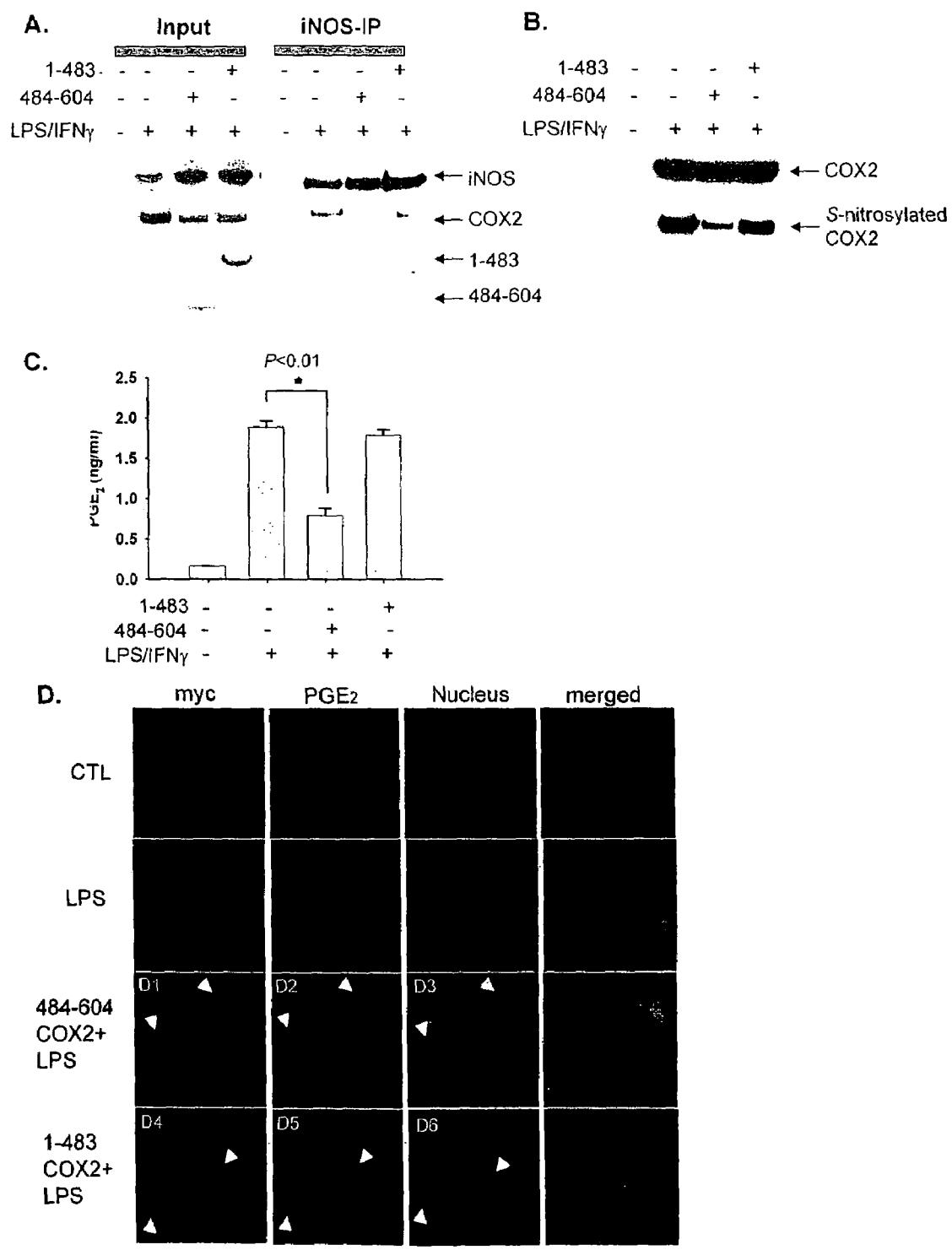

A.

B.

A.

|  | Input |  |  |  | in Switch |  |  |  |  |  |  |
|---|---|---|---|---|---|---|---|---|---|---|---|
| COX2-myc | − | + | + | + | − | + | + | + | + | + | + |
| GSNO(100μM) | − | − | + | − | − | − | − | + | + | − | − |
| H2O2(100μM) | − | − | − | + | − | − | − | − | − | + | + |
| Ascorbate(1mM) | − | − | − | − | − | − | + | + | − | + | − |
| Arsenite(10mM) | − | − | − | − | − | − | − | − | + | − | + |

← COX2

B.

|  | Input |  | Biotin Switch |  |  |  |
|---|---|---|---|---|---|---|
| LPS/IFNγ | − | + | − | − | + | + |
| Ascorbate(1mM) | − | − | + | − | + | − |
| Arsenite(10mM) | − | − | − | + | − | + |

← COX2

A.

B.

A.

B.

INDUCIBLE NITRIC OXIDE SYNTHASE BINDS, S-NITROSYLATES, AND ACTIVATES CYCLOOXYGENASE-2

This application claims the benefit of provisional application Ser. No. 60/675,552 filed Apr. 28, 2005, the disclosure of which is expressly incorporated herein.

The invention was made using funds from the U.S. government, grant numbers DA00266 and DA00074 from NIDA. Therefore, the U.S. government retains certain rights in the invention.

TECHNICAL FIELD OF THE INVENTION

This invention is related to the area of drug screening and therapeutics. In particular, it relates to anti-inflammatory agents.

BACKGROUND OF THE INVENTION

Cyclooxygenase-2 (COX2; prostaglandin $H_2$ synthase) and inducible nitric oxide (NO) synthase (iNOS) are two of the principal inflammatory mediators. (1, 2). Following inflammatory stimuli, these two enzymes, which are inactive under basal conditions, undergo new synthesis, respectively manufacturing large quantities of prostaglandins and NO. Needleman and associates had shown that NOS inhibitors can prevent the formation of prostaglandins (Salvemini et al., *PNAS* 90:7240, 1993). The simplest interpretation of these findings would be that NO, a free radical, gives rise to even more toxic free radicals such as peroxynitrite and hydroxide free radical, which constitute inflammatory stimuli that would lead to induction of COX2 and formation of prostaglandins.

COX2 inhibitors have attained widespread use as anti-inflammatory agents, though they elicit potentially adverse side effects (1, 3-5), while iNOS inhibitors are not presently employed therapeutically. Inflammatory stimuli elicit new synthesis of iNOS and COX2 proteins with similar time courses suggesting that the two systems may interact (6, 7). Stimulants of iNOS such as bradykinin (8) and lipopolysaccharide (LPS) plus interferon γ (IFNγ), components of endotoxin, also enhance prostaglandin formation (9).

There is a continuing need in the art to develop therapies for reducing disease conditions caused by or exacerbated by inflammation.

SUMMARY OF THE INVENTION

According to one embodiment of the invention a method is provided for screening for substances useful for relieving inflammation. A test substance is contacted with a first protein and a second protein under conditions in which the first protein and the second protein bind to each other. The first protein is selected from the group consisting of: mammalian iNOS, a fragment of mammalian iNOS from the N-terminal 10% of iNOS sufficient to bind COX2, and a fusion protein comprising said fragment of mammalian iNOS. The second protein is selected from the group consisting of mammalian COX2, a fragment of mammalian COX2 from the C-terminal 20% of COX2 sufficient to bind iNOS, and a fusion protein comprising said fragment of COX2. The amount of free or bound of said first or said second protein is determined. A test substance is identified as a candidate drug for relieving inflammation if it increases the amount of free first or second protein or decreases the amount of bound first or second protein.

Another aspect of the invention is a method of treating inflammation in a patient. An antibody which binds to amino acid residues 1-114 of mammalian iNOS or amino acid residues 484-604 or 488-604 of mammalian COX2 is administered to the patient. Binding of iNOS to COX2 is thereby inhibited in the patient.

Yet another embodiment of the invention is a method of treating inflammation in a patient. A nucleic acid vector encoding a polypeptide comprising a fragment of human iNOS from the N-terminal 10% of INOS sufficient to bind COX2 or a fragment of human COX2 from the C-terminal 20% of COX2 sufficient to bind iNOS, is administered to the patient. Binding of iNOS to COX2 is thereby inhibited in the patient.

A further aspect of the invention is a method of treating inflammation in a patient. A polypeptide comprising a fragment of human iNOS from the N-terminal 10% of iNOS sufficient to bind COX2 or a fragment of human COX2 from the C-terminal 20% of COX2 sufficient to bind iNOS, is administered to the patient. Binding of iNOS to COX2 is thereby inhibited in the patient.

Also provided by the present invention is a combination therapeutic agent. The combination agent comprises an inhibitor of COX2 and a protein binding inhibitory agent selected from the group consisting of: an antibody which binds to amino acid residues 1-114 of human iNOS or amino acid residues 484-604 of human COX2; a polypeptide comprising a fragment of human iNOS from the N-terminal 10% of iNOS sufficient to bind COX2 or a fragment of human COX2 from the C-terminal 20% of COX2 sufficient to bind iNOS; or a nucleic acid vector encoding a polypeptide comprising a fragment of human iNOS from the N-terminal 10% of iNOS sufficient to bind COX2 or a fragment of human COX2 from the C-terminal 20% of COX2 sufficient to bind iNOS.

These and other embodiments which will be apparent to those of skill in the art upon reading the specification provide the art with methods of identifying potential anti-inflammatory agents and with therapeutic anti-inflammatory agents.

BRIEF DESCRIPTION OF THE DRAWINGS

FIG. 1A-1H. COX2 and iNOS bind selectively in vitro and in intact cells. (FIG. 1A) RAW264.7 cells were induced with LPS(2 μg/ml)/IFNγ(100 U/ml). COX2 was immunoprecipitated by anti-COX2 antibodies and probed using anti-COX and anti-iNOS antibodies. (FIG. 1B and FIG. 1C) RAW264.7 cells were induced by LPS/IFNγ with or without an iNOS inhibitor 1400W (100 μM) or COX2 inhibitor SC58125 (100 μM). Cell lysates were subjected to immunoprecipitation with anti-COX2 and anti-iNOS antibodies. (FIG. 1D) The fragments of iNOS denoted in red bound to COX2, while fragments labeled purple did not as determined by co-immunoprecipitation. (FIG. 1E) HEK293T cells transfected with COX2 and GST-fused iNOS fragments were immunoprecipitated with GST conjugated beads. Proteins were detected by the addition of GST•HRP and goat anti-COX2 antibodies. (FIG. 1F) HEK293T cells transfected with COX2 and myc-tagged iNOS fragments were immunoprecipitated with anti-myc antibodies. (FIG. 1G) Generated fragments of COX2 which bind to full length iNOS are labeled in red, while those that do not bind are identified in yellow. (FIG. 1H) HEK293T cells transfected with iNOS and myc-tagged COX2 fragments were immunoprecipitated by anti-myc.

FIG. 2A-2G. S-nitrosylation of COX2 enhances enzyme activity. (FIG. 2A) COX2 expressed in HEK293T cells is S-nitrosylated in the presence of GSNO (100 μM) as determined by biotin switch assay. (FIG. 2B) LPS/IFNγ treatment of RAW264.7 cells elicits S-nitrosylation of COX2 which is subsequently prevented by the iNOS inhibitor 1400W (100 μM). (FIG. 2C) COX2 enzyme activity was measured from the cell lysate of COX2 transfected HEK293T cells in the presence or absence of SNP (200 μM) and ascorbate (ASC, 500 μM). Bars represent the mean±SE of three independent cell cultures performed in triplicate. (* Student's t-test) (FIG. 2D) Transfected COX2-myc is S-nitrosylated in the presence of SNP (200 μM) and reversed by the addition of 500 μM ASC. (FIG. 2E) COX2-myc expressed in HEK293T cells is S-nitrosylated by various concentration of GSNO. The dose-dependence of GSNO-mediated activation of PGE2 (ng/mL) was measured. Data were pooled from at least three independent determinations each in triplicate. (FIG. 2F) Recombinant human COX2 was treated with SNP (1 mM) and COX2 activities were measured. (n=3, ●=CTL, $V_{max}$=81.3±4.8 nmol/min/mg, $K_m$=16.2±2.2 μM; ○=1 mM SNP, $V_{max}$=132±6.5 nmol/min/mg, $K_m$=17.0±2.0 μM) (FIG. 2G) Recombinant human COX2 was treated with SNP (1 mM) and its turnover rate ($k_{cat}$) was measured in the presence of various concentration of sucrose. Data was expressed as Kcat-control over Kcat in each viscosity vs. viscosity ratio.

FIG. 3A-3D. Endogenously generated NO enhances COX2 activity. (FIG. 3A) RAW264.7 cells were activated by LPS/IFNγ at various concentrations of 1400W overnight. The dose dependence of 1400W mediated suppression of PGE2 (ng/mL) and nitrite (μM) levels were then measured. Data were pooled from at least three independent determinations each in triplicate. (* Student's t-test) (FIG. 3B) Combinations of L-NAME (500 μM), L-NAME+L-Arg (1 mM) or D-Arg (1 mM), and D-NAME (500 μM) were added to RAW264.7 cells subjected to LPS/IFNγ. PGE2 levels were measured and the data are pooled from three independent experiments performed each in triplicate. (FIG. 3C) PGE2 and nitrite levels were measured from wild type and iNOS knock-out primary peritoneal macrophages treated with or without LPS/IFNγ. (* Student's t-test) (FIG. 3D) S-nitrosylation of COX2 of wild type primary peritoneal macrophages treated with LPS/IFNγ, is abolished in iNOS knock-out cultures.

FIG. 4A-4D. COX2-myc fragment attenuates iNOS binding to COX2 and NO-mediated activation of PGE2 production. RAW264.7 cells transfected with COX2-myc fragments 1-483 and 484-604 were treated with LPS/IFNγ. (FIG. 4A) Cell lysates were immunoprecipitated with rabbit anti-iNOS antibodies and analyzed with mouse anti-iNOS, goat anti-COX2 and mouse anti-myc antibodies. (FIG. 4B) COX2-myc fragment (484-604) decreases S-nitrosylation of COX2 in RAW264.7 cells. (FIG. 4C) RAW264.7 cells were transfected with the fragments and treated with LPS/IFNγ. PGE2 levels were measured and the data are pooled from three independent experiments performed each in triplicate. (* Student's t-test) (FIG. 4D). PGE2 and COX2 fragments were visualized with confocal microscopy using mouse anti-myc and Rabbit anti-PGE2 antibodies. Images of COX2 (red) and PGE2 (green) were superimposed to show co-localization. Nuclei were visualized using Hoechst staining (blue). In FIG. 4D1 arrows point to two RAW264.7 cells, only one of which is transfected with the COX2 fragment 484-604 (red). In FIG. 4D2, the same two cells are analyzed for presence of endogenous PGE2 produced after activation of RAW264.7 cells by LPS/IFNγ treatment. Immunofluorescent staining shows a reduction in the PGE2 expression level in the COX2-myc 484-604 transfected cell compared to the non-transfected cell (FIG. 4D2). This observation contrasts with FIG. 4D4 whose arrows point to a transfected and non-transfected cell of the COX2 fragment 1-483. Unlike FIG. 4D2, FIG. 4D5 does not show a reduction of PGE2 in the transfected cell as compared to the non-transfected cell.

(FIG. 5A) HEK293T cells transfected with COX2, and iNOS were subjected to immunoprecipitation with anti-myc antibody and analyzed with mouse anti-iNOS and goat anti-COX2 antibodies. (FIG. 5B) Peritoneal macrophages were obtained either 4 or 22 hours after 3% thioglycolate injection. Cell lystes were immunoprecipitated by rabbit anti-iNOS antibody and analyzed with rat anti-COX2 and mouse anti-iNOS antibodies.

(FIG. 6A) GST-tagged iNOS fragments for amino acid residues 1-500 and 1-525 were respectively combined with full length COX2 and pulled down using GST beads. Purified GST was also combined with COX2 as a control. (FIG. 6B) GST-tagged iNOS fragments for amino acid residues 1-500 and 510-1145 were co-immunoprecipitated with COX2 using GST pull down. These results suggest that interaction between iNOS and COX2 is direct binding.

(FIG. 7A) COX2 is selectively S-nitrosylated in the presence of additional NO donors DETA-NO (500 μM), SNP (100 μM), and Spermine-NO (100 μM) using the biotin switch assay. (FIG. 7B) S-nitrosylation of COX2 in RAW264.7 cells treated with LPS/IFNγ was S-nitrosylated using fluorometic detection assay, which was abolished by iNOS specific inhibitor, 1400W.

(FIG. 8A) COX2 transfected in HEK293T cells were treated with either GSNO or H2O2 to generate S-nitrosothiol or sulfenic acid, respectively. It has been known that 10 mM arsenite is a reducing reagent specific for sulfenic acid. Biotin switch assay was performed with either 1 mM ascorbate or 10 mM sodium arsenite. Our results show that ascorbate is specific for S-nitrosylated COX2 not for COX2 with sulfenic modification, which was confirmed by reversing it using sodium arsenite. (FIG. 8B) S-nitrosylation of COX2 in RAW264.7 cells treated with LPS/IFNγ was confirmed using biotin switch assay either with ascorbate or sodium arsenite. Ascorbate treatment reversed COX2 modification in RAW264.7 cells treated with LPS/IFNγ but sodium arsenite did not, showing that COX2 in LPS/IFNγ-treated RAW264.7 cells is mostly S-nitrosylated.

(FIG. 9A) HEK293T cells transfected with COX2-myc were treated with 100 μM GSNO for 3 hours with or without oxyhemoglobin and biotin switch assay was performed. Oxyhemoglobin blocked GSNO-mediated S-nitrosylation of COX2. (FIG. 9B) However, oxyhomoglobin did not prevent S-nitrosylation of COX2 in RAW264.7 cells induced by LPS/IFNγ suggesting that a delivery of NO to COX2 is crucial.

(FIG. 10A) COX2 has 13 cysteines and we mutated all the cysteines to serine, two of which were not expressed.

Single mutation of cysteine to serine did not eliminate S-nitrosylation signal by the biotin switch assay (data shown) suggesting that there are more than one cysteine can be S-nitrosylated. Hence, we performed biotin switch assay using COX2 fragments and demonstrated that the target for S-nitrosylation is located in c-terminal region (484-604). (FIG. 10B) We wondered which of the 13 cysteines of COX2 are critical for the S-nitrosylation elicited augmentation of COX2 activity. COS1 cells were transfected with empty vector, wild type, or mutants of COX2-myc. Cells were treated with (red) or without (black) NO donor for 3 h, at which point $PGE_2$ levels were measured. Mutation of C526 to serine (C526S) abolishes stimulation of $PGE_2$ formation by the NO donor SNP, while C561S fails to influence stimulation. The target cysteine which is responsible for NO-mediated COX2 activation is also located in the region of 484-604. We attempted to study COX2 with mutation of the other 11 cysteines, two of which could not be expressed in COS1 cells while the other 9 mutations had no demonstrable catalytic activity even under control conditions (data not shown). We could not eliminate the possibility that there is more than one S-nitrosylation target but identified the target cysteine responsible for NO-mediated activation of COX2.

DETAILED DESCRIPTION OF THE INVENTION

Figure 1:
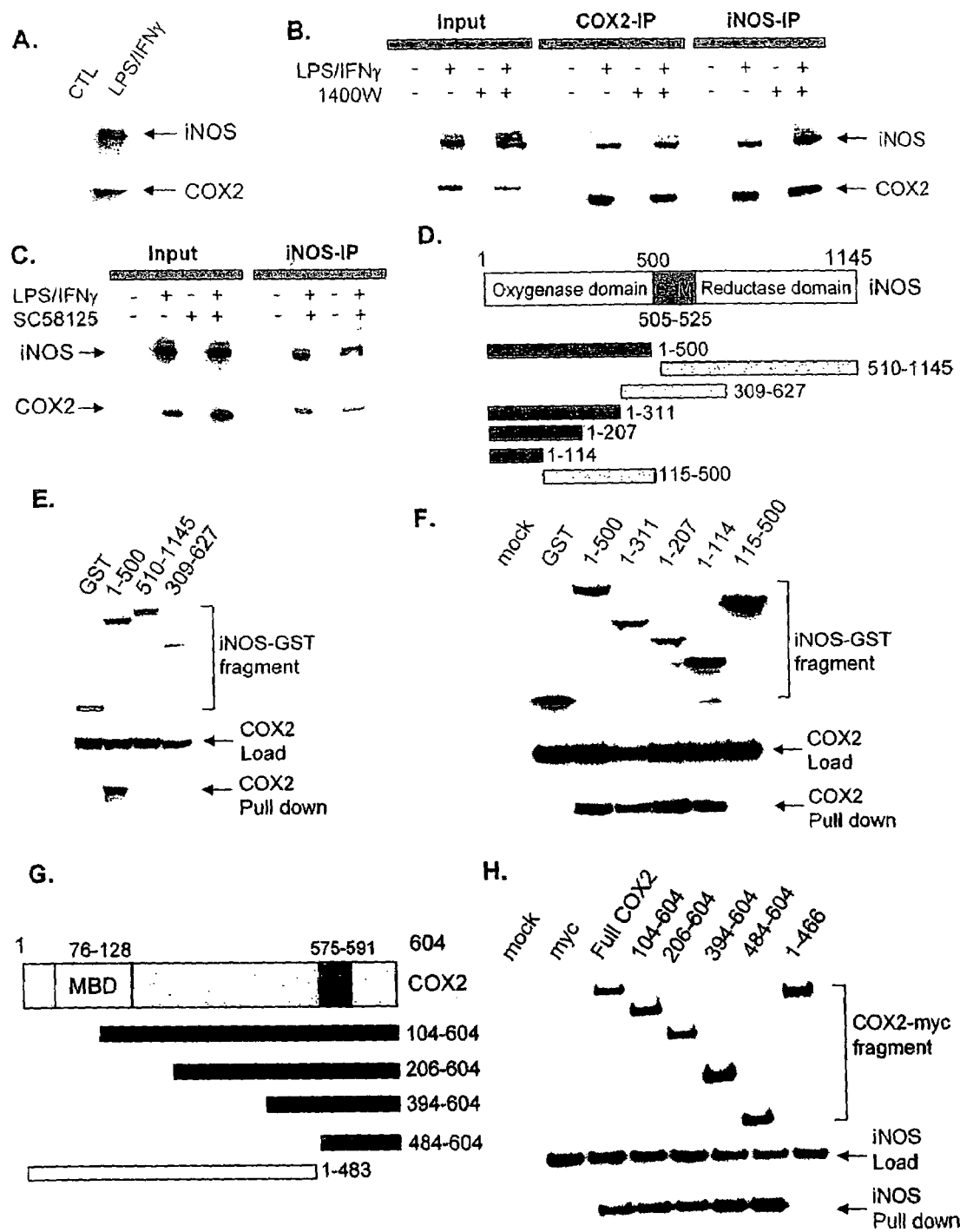

The inventors have found that iNOS binds directly to COX2 without a scaffold protein. Moreover, we found that iNOS binding to COX2 leads to S-nitrosylation and activation of COX2. We further found that the binding of iNOS to COX2 leads to augmented formation of prostaglandins by COX2. Based on these findings, one can screen and develop novel anti-inflammatory drugs by monitoring the ability of candidate drugs to inhibit the binding of iNOS to COX2. Peptide agents that mimic the portions of the two binding partners that interact with each other, can be used to block the activation of COX2 by iNOS. Similarly antibodies which bind to the interacting portions of the binding partners can be use to inhibit inflammation responses.

For screening assays, any molecules comprising the binding domains of COX2 and iNOS can be used. These include full-length COX2 and iNOS polypeptides, fragments comprising the binding domains of the two full-length polypeptides, fusion proteins comprising the binding domains of the two full length polypeptides. As defined experimentally, the binding domains are within the N-terminal 10% of iNOS and the C-terminal 20% of COX2, as these residues have been found to be sufficient to mediate binding. Fragments contain less than the full-length proteins, typically less than 50%, more typically less than 25%. Fragments of COX2 do not contain the membrane binding domain while fragments of iNOS do not contain the reductase or CaM (calmodulin) domains. Any of these forms of iNOS protein can be used to bind to any form of the COX2 protein. Binding can be determined by measuring one or both of the binding partners, either in the bound or the free form. Increase in the bound form or decrease in the free form indicates binding of the two partners. Conversely, added test compounds which inhibit binding can be characterized by the decrease in bound form or increase in free form of one or both of the binding partners.

For screening assays, the test compound is preferably a small molecule that binds to and occupies, for example, the binding site of the COX2 or iNOS polypeptide, such that normal binding of the two binding partners is prevented. Examples of such small molecules include, but are not limited to, small peptides or peptide-like molecules. Any small organic molecule can be used. Libraries of natural or synthetic compounds can be screened. Small molecules which mimic three dimensional structure of peptides can be designed.

In screening assays, either the COX2 or iNOS polypeptide can comprise a detectable label, such as a fluorescent, radioisotopic, chemiluminescent, or enzymatic label, such as horseradish peroxidase, alkaline phosphatase, or luciferase. Detection of bound COX2 or iNOS polypeptide can then be accomplished, for example, by direct counting of radioemmission, by scintillation counting, or by determining conversion of an appropriate substrate to a detectable product.

Alternatively, inhibition of binding of a human COX2 to an iNOS polypeptide by a test compound can be determined without labeling the interactants. For example, a microphysiometer can be used to detect binding of a human COX2 and iNOS polypeptide. A microphysiometer (e.g., Cytosensor™) is an analytical instrument that measures the rate at which a cell acidifies its environment using a light-addressable potentiometric sensor (LAPS). Changes in this acidification rate can be used as an indicator of the interaction between a human COX2 or iNOS polypeptide (McConnell et al., *Science* 257, 1906-1912, 1992).

Determining the ability of a mammalian COX2 and an iNOS polypeptide to bind also can be accomplished using a technology such as real-time Bimolecular Interaction Analysis (BIA) (Sjolander & Urbaniczky, *Anal. Chem.* 63, 2338-2345, 1991,and Szabo et al., *Curr. Opin. Struct. Biol.* 5, 699-705, 1995). BIA is a technology for studying biospecific interactions in real time, without labeling any of the interactants (e.g., BIAcore™). Changes in the optical phenomenon surface plasmon resonance (SPR) can be used as an indication of real-time reactions between biological molecules.

In yet another aspect of the invention, a mammalian COX2 or iNOS polypeptide can be used in a two-hybrid assay or three-hybrid assay (see, e.g., U.S. Pat. No. 5,283, 317; Zervos et al., *Cell* 72, 223-232, 1993; Madura et al., *J. Biol. Chem.* 268, 12046-12054, 1993; Bartel et al., *BioTechniques* 14, 920-924, 1993; Iwabuchi et al., *Oncogene* 8, 1693-1696, 1993; and Brent W094/10300), to identify agents which inhibit binding of the COX2 and iNOS polypeptides and thereby modulate COX2 activity.

The two-hybrid system is based on the modular nature of most transcription factors, which consist of separable DNA-binding and activation domains. Briefly, the assay utilizes two different DNA constructs. For example, in one construct, polynucleotide encoding a mammalian COX2 or iNOS polypeptide can be fused to a polynucleotide encoding the DNA binding domain of a known transcription factor (e.g., GAL-4, particularly yeast GAL-4). In the other construct a DNA sequence that encodes the other of COX2 or iNOS can be fused to a polynucleotide that codes for the activation domain of the known transcription factor. When the fusion proteins are able to interact in vivo to form a protein-dependent complex, the DNA-binding and activation domains of the transcription factor are brought into close proximity. This proximity allows transcription of a reporter gene (e.g., LacZ, particularly *E. coli* LacZ), which is operably linked to a transcriptional regulatory site responsive to the transcription factor. Contacting such cells (typically but not limited to yeast cells) with test substances will permit an assay for binding inhibition. Expression or inhibition of expression of the reporter gene can be detected, thus identifying an agent which inhibits the interaction of COX2 and iNOS polypeptide.

It may be desirable to immobilize either the COX2 or iNOS polypeptide or the test compound to facilitate separation of bound from unbound forms of one or both of the interactants, as well as to accommodate automation of the assay. Thus, either the COX2 or iNOS polypeptide or the test compound can be bound to a solid support. Suitable solid supports include, but are not limited to, glass or plastic slides, tissue culture plates, microtiter wells, tubes, silicon chips, or particles such as beads (including, but not limited to, latex, polystyrene, or glass beads). Any method known in the art can be used to attach the polypeptide or test compound to a solid support, including use of covalent and non-covalent linkages, passive absorption, or pairs of binding moieties attached respectively to the polypeptide or test compound and the solid support. Test compounds can be bound to the solid support in an array, so that the location of individual test compounds can be tracked. Binding of a test compound to a mammalian COX2 or iNOS polypeptide can be accomplished in any vessel suitable for containing the reactants. Examples of such vessels include microtiter plates, test tubes, and microcentrifuge tubes.

In one embodiment, the iNOS polypeptide is a fusion protein comprising a domain that allows the iNOS polypeptide to be bound to a solid support. For example, glutathione-S-transferase fusion proteins can be adsorbed onto glutathione sepharose beads (Sigma Chemical, St. Louis, Mo.) or glutathione derivatized microtiter plates, which are then combined with the test compound or the test compound and the non-adsorbed COX2 polypeptide; the mixture is then incubated under conditions conducive to complex formation (e.g., at physiological conditions for salt and pH). Following incubation, the beads or microtiter plate wells are washed to remove any unbound components. Binding of the interactants can be determined either directly or indirectly, as described above. Alternatively, the complexes can be dissociated from the solid support before binding is determined. In another alternative, the COX2 polypeptide is a fusion protein.

Other techniques for immobilizing proteins on a solid support also can be used in the screening assays of the invention. For example, either an iNOS or COX2 polypeptide or a test compound can be immobilized utilizing conjugation of biotin and streptavidin. Biotinylated iNOS or COX2 polypeptides test compounds can be prepared from biotin-NHS(N-hydroxysuccinimide) using techniques well known in the art (e.g., biotinylation kit, Pierce Chemicals, Rockford, Ill.) and immobilized in the wells of streptavidin-coated 96 well plates (Pierce Chemical). Alternatively, antibodies which specifically bind to an iNOS or COX2 polypeptide, or a test compound, but which do not interfere with a desired binding site, can be derivatized to the wells of the plate. Unbound target or protein can be trapped in the wells by antibody conjugation.

Methods for detecting such complexes, in addition to those described above for the GST-immobilized complexes, include immunodetection of complexes using antibodies which specifically bind to the iNOS or COX2 polypeptide or test compound, enzyme-linked assays which rely on detecting an activity of the iNOS or COX2 polypeptide, and SDS gel electrophoresis under non-reducing conditions.

Screening for test compounds which bind to an iNOS or COX2 polypeptide also can be carried out in an intact cell, in whole animals, or cell-free systems. Any cell which comprises an iNOS or COX2 polypeptide can be used in a cell-based assay system. An iNOS or COX2 polynucleotide can be naturally occurring in the cell or can be introduced using techniques such as those described above. Binding of the test compound to an iNOS or COX2 polypeptide is determined as described above.

Once a test compound has been identified that inhibits the binding of iNOS to COX2, whether in cells, in whole animals, or in a cell-free system, it can be further tested to determine its effect on inflammation. For example, it can be tested for its effect on prostaglandin synthesis or for its effect in any of several animal models of inflammation known in the art. Exemplary animal models include the following mouse strains, without limitation. The mouse strain CD1-Tg(Gadd45β-luc)-Xen (Gadd45β-luc LPTA®) animal model is useful in studying apoptosis, Gadd45β gene regulation, MAP kinase- and NF-κB mediated signaling pathways, and the treatment of inflammatory diseases and cancer. The mouse strain FVB/N-Tg(iNos-luc)Xen (iNos-luc LPTA®) animal model is useful in studying sepsis, arthritis, and anti-inflammatory compounds. The mouse strain FVB/N-Tg(Epx-luc)-Xen (Epx-luc LPTA®) animal model is useful in studying changes in eosinophil production resulting from parasite infection and asthma, and may be used as donor animals for studying bone marrow transplantation. The mouse strain BALB/C-Tg(Saa1-luc)-Xen (Saa1-luc LPTA®) animal model is useful in studying sepsis, arthritis, amyloidosis, and A-SAA-mediated disorders. The mouse strain CD1-Tg(IL2-luc)-Xen (IL2-luc LPTA®) animal model is useful in studying IL-2 gene regulation, inflammatory diseases, and cancer. The mouse strain BALB/C-Tg(Tnfα-luc)-Xen (Tnfα-luc LPTA®) animal model is useful in studying sepsis, arthritis, inflammatory bowel disease, apoptosis, TNFα gene regulation, and the treatment of TNFα-mediated inflammatory diseases. The mouse strain BALB/C-Tg(NFκB-RE-luc)-Xen (NFκB-RE-luc LPTA® animal model is useful in studying sepsis, arthritis, inflammatory bowel disease, apoptosis, tumor development, NFκB gene regulation, and the treatment of inflammatory diseases and cancer. The mouse strain DBA/1,BALB/C-Tg (NFκB-RE-luc [Oslo])-Xen (NFκB-luc (Oslo) LPTA®) animal model is useful in studying sepsis, arthritis, inflammatory bowel disease, apoptosis, tumor development, NFκB gene regulation, and the treatment of inflammatory diseases and cancer. The mouse strain BALB/C-Tg(IkBa-luc)-Xen (IκBα-luc LPTA®) animal model is useful in studying sepsis, arthritis, inflammatory bowel disease, apoptosis, tumor development, transcriptional regulation of IκBα gene and other genes responsive to NFκB, and the treatment of inflammatory diseases and cancer. Any animal model of inflammation can be used.

COX2 and iNOS for use in any of the methods or compositions of the invention can be from any species, particularly from mammals, such as rat, mouse, rabbit, dog, cat, and most particularly from humans. These proteins are well known in the art and a version of these proteins from any individual can be used even though the version of the protein from that individual may vary slightly from that which is documented in a protein sequence database. Exemplary sequences which can be used are those which are documented at GenBank as P35228 and P35354. Other COX2 sequences which can be used include those from *P. troglodytes, C. familiaris, M musculus, R. norvegicus*, and *G. gallus*, horse and sheep. Exemplary sequences include AAH52900 (mouse), NP_000954 (human), NP_058928 (*Rattus norvegicus*), P79208 (sheep), O62698 (bovine), O19183 (horse), and NP_001003354 (*Canis familiaris*). Other iNOS sequences which can be used include those from *C. familiaris, M. musculus, R. norvegicus*, and *G.*

*gallus*. Exemplary sequences include NP_001003186, NP_035057, and NP_990292, respectively. All referenced protein and/or gene sequences are incorporated by reference herein as they exist on Apr. 28, 2006.

Treatment modalities based on the discovery of binding of iNOS and COX2 include administration of a polypeptide, administration of a nucleic acid encoding a polypeptide, and administration of an antibody. The nucleic acid can be a naturally occurring genomic or cDNA sequence or can be any sequence which encodes the desired protein. Each of these is designed to inhibit binding of the two binding partners. Both the polypeptides and the antibodies bind to the portion of the binding partners that interact, thereby inhibiting the interaction. Inhibition of the interaction inhibits the iNOS-mediated S-nitrosylation of COX2 which activates COX2. Polypeptides delivered directly or indirectly via nucleic acids can be fragments of fusion proteins comprising a binding domain or sufficient amounts of a binding domain to bind and interferen with COX2/iNOS binding.

Inflammation which can be treated according to the present invention includes any which is exacerbated by prostaglandin synthesis. These include, without limitation, chronic inflammatory diseases, such as rheumatoid arthritis, inflammatory bowel disease, systemic lupus erythematosus, multiple sclerosis, type 1 diabetes, rheumatoid arthritis, chronic obstructive pulmonary disease (COPD), asthma, allergic rhinitis, cardiovascular disease, psoriasis. Inflammatory diseases of the brain include abscess, meningitis, encephalitis and vasculitis. Any of these diseases can be treated according to the methods of the present invention.

Antibodies for use in the present invention can be monoclonal or polyclonal. They can gain their specificity by purification or by limitation of the inducing immunogen. The antibodies will bind to the N-terminal 10% of iNOS or to the C-terminal 20% of COX2. Administration of antibodies can be by any means known in the art, but typically the antibodies are administered by injection, such as intrathecal, intraventricular, intravascular (intravenous or intraarterial), subcutaneous, intramuscular, intraperitoneal, intrapleural, by perfusion through a regional catheter, or by direct intralesional injection. When administering antibodies by injection, the administration may be by continuous infusion or by single or multiple boluses. Polypeptides and polynucleotides can be administered by similar means.

In general, the dosage of administered antibodies will vary depending upon such factors as the patient's age, weight, height, sex, general medical condition, and previous medical history. Preferably, a saturating dose of antibody is administered to a patient. Antibodies can be administered as whole IgG, F(ab')$_2$, F(ab)$_2$, Fab', or Fab.

Typically, it is desirable to provide the recipient with a dosage of antibody that is in the range of from about 50 to 500 milligrams of antibody, although a lower or higher dosage also may be administered as circumstances dictate. Effective in vivo dosages of an antibody are in the range of about 5 mg to about 50 mg/kg, about 50 mg to about 5 mg/kg, about 100 mg to about 500 mg/kg of patient body weight, and about 200 to about 250 mg/kg of patient body weight. High doses of antibody may cause anaphylaxis due to complement activation with endogenous antibodies. This side effect, however, can be prevented by administration of oligosaccharides that bind with endogenous antibodies, as detailed below.

The antibodies of the present invention can be formulated according to known methods to prepare pharmaceutically useful compositions, whereby antibodies are combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. See, for example, Remington's Pharmaceutical Sciences, 19th Ed. (Mack Publishing Co. 1995), and Gilman's The Pharmacological Basis of Therapeutics, 7th Ed. (MacMillan Publishing Co. 1985).

For purposes of therapy, an antibody and a pharmaceutically acceptable carrier are administered to a patient in a therapeutically effective amount. A combination of an antibody and a pharmaceutically acceptable carrier is said to be administered in a "therapeutically effective amount" if the amount administered is physiologically significant. An agent is physiologically significant if its presence results in a detectable change in the physiology of a recipient patient. In the present context, an agent is physiologically significant if its presence results in the modulation of an immune response or malignant T cell malignancy growth.

Polynucleotides can be administered in any vector, whether viral or non-viral designed for delivery and expression of inserted nucleic acid sequences. Polynucleotides and/or proteins can be further formulated in liposomes or cationic vesicles or particles for added stability. Viral vectors include adenovirus vectors, adeno-associated virus vectors, retrovirus vectors, lentivirus vectors. Non-viral vectors include plasmid vectors. Exemplary types of viruses include HSV (herpes simplex virus), AAV (adeno associated virus), HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers.

Inducible NOS and COX2 physiologically bind, bringing NO in proximity with COX2, facilitating its S-nitrosylation and activation. Earlier findings that NOS inhibition decreases prostaglandin formation suggested a relationship between the two systems(10, 26), but might have reflected a generally diminished stressful stimulus to the COX2 system rather than a direct intermolecular linkage. Because NO is a labile molecule which can be rapidly inactivated within cells by the high physiologic concentrations of glutathione or other reducing agents, it is possible that many of NO's physiologic actions will require delivery of NO to its targets (15). Other instances of NO delivery have primarily involved nNOS acting via scaffold proteins. Thus, a scaffold protein CAPON links nNOS to Dexras1 and provides NO to S-nitrosylate Dexras1 and act as its guanine nucleotide exchange factor(27). Similarly the scaffold protein PSD95 links nNOS to N-Methyl-D-aspartate (NMDA) receptors where NO S-nitrosylates and inactivates NMDA receptors (28). In contrast to these examples, iNOS binds directly to COX2 with no intervening scaffold protein. A similar direct delivery of a regulatory metabolite via protein-protein interactions involves the binding of glyceraldehyde-3-phosphate dehydrogenase(GAPDH) to inositol 1,4,5-trisphosphate (IP3) receptors with NADH formed by GAPDH selectively augmenting calcium release activity of IP3 receptors(29).

The molecular synergism between iNOS and COX2 may represent a major mechanism of inflammatory responses. Inhibitors of iNOS do relieve fever and pain, classically associated with prostaglandin production which may reflect the iNOS—COX2 interaction, though such actions are sufficiently indirect that one cannot draw strong conclusions (30, 31).

Our findings have therapeutic relevance. Thus drugs which block the iNOS—COX2 interaction might have anti-inflammatory action. Moreover, such agents might synergize with COX2 inhibitor drugs permitting lower doses with less side-effects. While it has been speculated that adverse cardiovascular effects of COX2 inhibitors reflect inhibition of $PGE_2$ formation, this has not been directly established so that other actions of the drugs might be involved(32).

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

EXAMPLE 1

Materials and Methods

Materials and Methods

Cells. HEK293T, COS1 and RAW 264.7 murine macrophages were obtained from the American Type Culture Collection (Manassas, Va.). They were grown in a humid atmosphere of 95% air and 5% CO2 at 37° C. in Dulbecco's modified Eagle's medium supplemented with 10% fetal bovine serum, L-glutamine (300 ug/ml), penicillin (100 U/ml), and streptomycin (100 μg/ml).

Preparation of peritoneal macrophages. Peritoneal macrophages were obtained following intraperitoneal injection of 1.5 ml of 3% sterile thioglycolate medium. After 4 days mice were sacrificed and macrophages were harvested as described(1).

Plasmid Constructions. Full length human cyclooxygenase2-encoding gene (gene bank sequence NM_000963) was purchased from ATCC in pCMV•SPORT6 vector. The sequence was amplified by PCR using primers harboring Sal1/Not1 restriction sites and cloned into the pCMV-Myc vector (Clontech, Palo Alto, Calif.). The murine inducible nitric oxide synthase (accession number NM_010927) cloned into the pcDNA3.1+vector (Invitrogen, Carlsbad, Calif.).

Immunoprecipitation. For co-immunoprecipitation experiments, $1\times10^6$ HEK293T cells were plated in 10 cm$^2$ culture dishes (Invitrogen, Carlsbad, Calif.). Cells were transfected with 4 μg pCMV•Myc-COX2, 2 ug pcDNA3.1-iNOS, or empty pCMV•Myc vector using LipofectAMINE PLUS (Invitrogen, Carlsbad, Calif.) according to the manufacturer's protocol. After 48 h, cells were harvested and lysed in ice-cold lysis buffer (100 mM Tris pH 7.4, 150 mM NaCl, 10% glycerol, 1% Triton X-100,and complete protease inhibitors). The supernatants (800 ul) from the HEKT cell extracts were pre-cleaned for non-specific binding with 50 ul protein A-Sepharose, then mixed overnight at 4° C. with 2 ug/ml anti-Myc antibody (Roche, Alameda, Calif.). After the addition of 80 μl of protein A-Sepharose, the immunoprecipitates were mixed for another 1 h at 4° C. The mixture was washed three times with the buffer described above and the pellet boiled in 10 ul SDS-loading dye, which was subjected to 6% SDS PAGE gel run in MOPS buffer. The proteins were then transferred to nitrocellulose membrane. The bands were visualized by ECL reagent (Pierce, Milwaukee, Wis.) as described by the manufacturer.

Site Directed Mutagenesis. The QuickChange site-directed mutagenesis system (Stratagene, La Jolla, Calif.) was employed per manufacturer's instructions to alter the thirteen cysteine residues in COX2 to serine. Each mutant was verified via automated sequencing by the Hopkins Core Facility.

S-nitrosylation assay. Cells were homogenized by 26G needle in HEN (250 mM Hepes-NaOH pH 7.7, 1 mM EDTA, 0.1 mM Neocuproine) buffer and then centrifuged at 1000 g for 10 min at 4° C. Cells lysates (240 μg) was added 4 vol of blocking buffer (9 vol of HEN buffer plus 1 vol 25% SDS, adjusted to 20 mM MMTS with a 2 M stock prepared in dimethylformamide (DMF)) at 50° C. for 20 min with frequent vortexing. The MMTS was then removed by desalting three times with the MicroBioSpin6 column (Bio-Rad, Hercules, Calif.) pre-equilibrated in HEN buffer. To the eluate was added biotin-HPDP prepared fresh as a 4 mM stock in DMSO from a 50 mM stock suspension in DMF. Sodium ascorbate was added to a final concentration of 1 mM. After incubation for 1 h at 25° C., biotinylated proteins were precipitated by streptavidin-agarose beads. The streptavidin-agarose was then pelleted and washed 5 times using HENS buffer. The biotinylated proteins were eluted by SDS-PAGE sample buffer and subjected to Western-blot analysis.

Fluorometric detection of S-nitrosothiols. The methods were modified according to Cook et al.(2) RAW264.7 cells were treated with LPS/IFNγ for overnight and COX2 was immunoprecipitated by donkey anti-rat COX2 antibodies. After that the samples were reacted with 100 μM 2,3-diaminonaphthalene (DAN) in the presence of 100 μM of HgCl2 and incubated in darkness for 30 min at room temperature. The generated fluorescent compound 2,3-napththyltrazole (NAT) was then measured at an excitation wavelength of 375 nm and an emission wavelength of 450 nm.

COX2 enzymatic assay. Recombinant human COX2 was obtained from Cayman Biochemical Inc. COX2 was treated with NO donor, SNP for 30 min and was then passed through a spin column (Bio-Rad, Hercules, Calif.) to remove excess NO. COX2 enzymatic activity was measured with a COX assay kit (Cayman Biochemical Inc, Ann Arbor, Mich.) according to the manufacturer's instructions.

Measurement of $PGE_2$. Cells were washed with worm PBS (×2) and incubated in the phenol free Dulbecco's modified Eagle's medium supplemented with 20 μM arachidonic acid and 3% albumin for 20 min. Media was collected and PGE2 production was measured with a $PGE_2$ ELISA kit from Assay Design (Ann Arbor, Mich.) according to the manufacturer's instructions.

Immunohistochemistry. RAW264.7 cells were transfected with deletion constructs of COX2. Cells were fixed in 4% paraformaldehyde in PBS for 5 min, permeablized in 0.1% Triton X-100 for 10 s, and then rinsed twice in PBS. Coverslips were then blocked in 10% goat serum at room temperature for 1 h and incubated with $PGE_2$ (Cayman Biochemical Inc, Ann Arbor, Mich.) and myc antibodies for 24 hr at 4° C. Rhodamine or fluorescein-conjugated secondary antibodies (Jackson Immunochemicals, West Grove, Pa.) were then added at 10 μg/ml for 1 hr at room temperature as indicated. Coverslips were mounted in ProLong (Molecular Probes, Eugene, Oreg.). Confocal microscopy, in which the immunofluorescent staining is superimposed on phase contrast images, employed a Noran OZ (Noran Instruments, Middleton, Wis.) confocal laser-scanning system, fitted to an Olympus IX-50 fluorescence microscope.

Viscosity studies. Viscosity experiments were performed with sucrose (0-31% w/w) as described previously (3, 4).

1. Nunoshiba, T., deRojas-Walker, T., Wishnok, J. S., Tannenbaum, S. R. & Demple, B. Activation by nitric oxide of an oxidative-stress response that defends *Escherichia coli* against activated macrophages. *Proc Natl Acad Sci USA* 90, 9993-7 (1993).

2. Cook, J. A., Kim, S. Y., Teague, D., Krishna, M. C., Pacelli, R., Mitchell, J. B., Vodovotz, Y., Nims, R. W., Christodoulou, D., Miles, A. M., Grisham, M. B., & Wink, D. A. Convenient colorimetric and fluorometric assays for S-nitrosothiols. *Anal Biochem* 238, 150-158 (1996).
3. Cole, P. A., Burn, P., Takacs, B., Walsh, C. T. Evaluation of the catalytic mechanism of recombinant human Csk (C-terminal Src kinase) using nucleotide analogs and viscosity effects. *J Bio Chem* 269, 30880-30887 (1994).
4. Brouwer, A. C., and Kirsch, J. F. Investigation of diffusion-limited rates of chymotrypsin reactions by viscosity variation. *Biochem* 21, 1302-1307 (1982)

EXAMPLE 2 iNOS and COX2 Bind in Vivo in Cells and Whole Animals

Figure 5A:
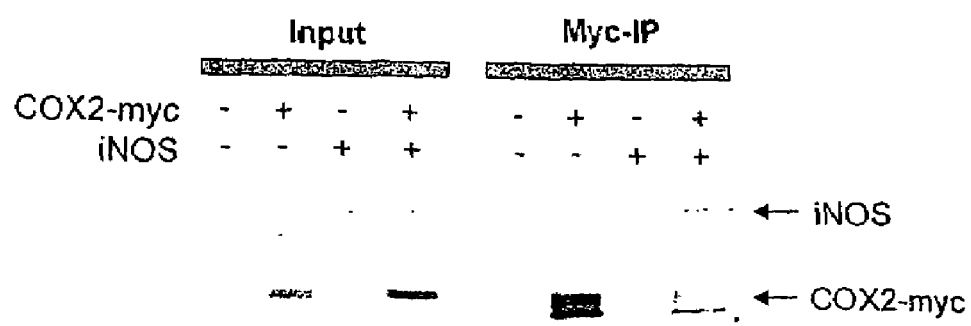
FIG. 5A-5B. (S1) COX2 and iNOS bind in vivo.

For initial studies we employed RAW264.7 cells, a macrophage cell line in which LPS and IFNγ massively activate both iNOS and COX2. In LPS/IFNγ treated cells immunoprecipitation with COX2 antibodies leads to co-precipitation of iNOS (FIG. 1A). Coprecipitation of COX2 and iNOS is also evident in HEK293T cells transfected with both proteins (FIG. 5A).

Figure 5B:
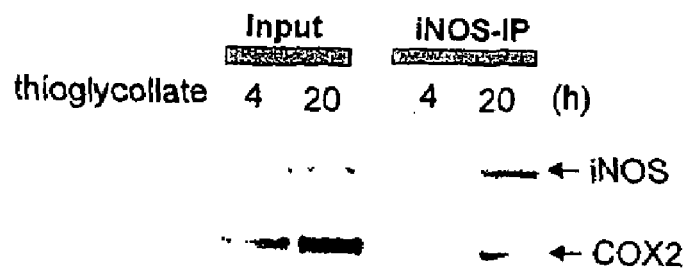
Figures 6A, 6B:
FIG. 6A-6B (S2.) GST-tagged iNOS fragments co-immunoprecipitate with COX2 in vitro.

To examine interactions between the two enzymes in intact organisms, we injected mice with thioglycollate, an inflammatory stimulus which typically produces peritonitis or pleuritis, and observed coprecipitation of iNOS and COX2 (FIG. 5B).

To determine whether catalytic activity of the enzymes influences their binding interactions, we co-precipitated the two proteins with iNOS antibodies or COX2 antibodies and examined the effect of the iNOS-selective inhibitor 1400W (FIG. 1B) or the COX2 selective inhibitor SC58125 (FIG. 1C). Co-precipitation of iNOS and COX2 is unaffected by either iNOS or COX2 inhibitors. The binding of iNOS and COX2 is selective, as we do not detect immunoprecipitation of COX1 with iNOS (data not shown).

EXAMPLE 3

Mapping the Binding Sites on the Two Interacting Proteins

To map the binding sites, we employed selective deletions of iNOS (FIG. 1D-F) and COX2 (FIG. 1G and H) sequences. Amino acids 1-114 appear to be the minimal portion of iNOS mediating binding, while amino acids 484-604 of COX2 are required. The binding area of iNOS occurs within the oxygenase domain, while the C-terminal portion of COX2 that mediates binding includes a COX2 domain which does not exist in COX1.

EXAMPLE 4

NO Donors Elicit S-nitrosylation of COX2

The two major mechanisms whereby NO influences its targets are stimulation of guanylyl cyclase by direct binding of NO to iron in heme at the active site of guanylyl cyclase(11, 12) or S-nitrosylation of protein targets on appropriate cysteines(13-15). Since COX2 possesses heme at its active site(16), this would be a potential target. However, NO binding to heme in COX does not alter its activity(17).

Figures 7A, 7B:
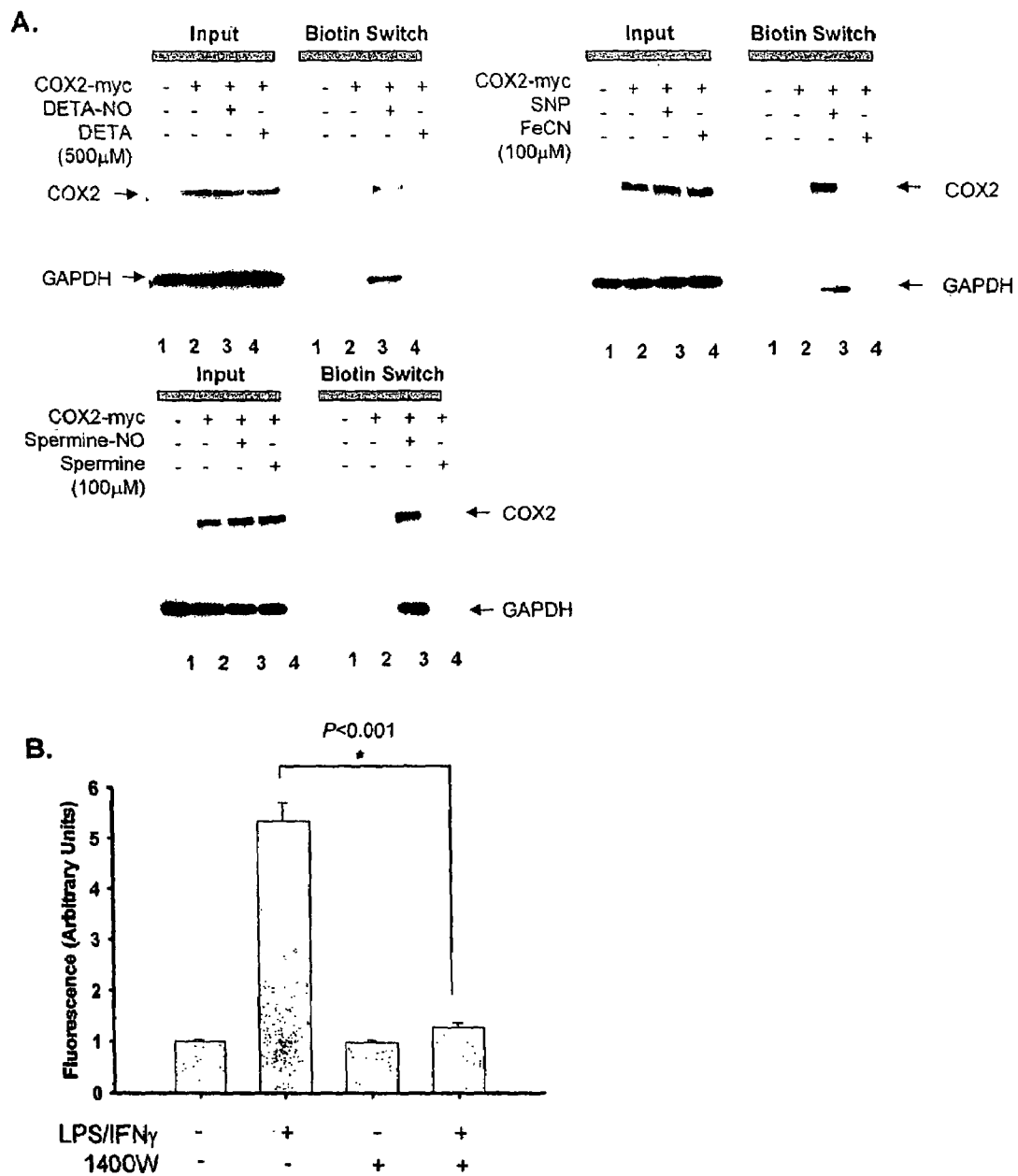
FIG. 7A-7B (S3.) COX2 is S-nitrosylated by NO in vitro and in vivo.

COX2 also contains 13 cysteines whose roles are not fully understood(18, 19). Hence, we explored the possibility of S-nitrosylation of COX-2 by NO, examining multiple NO donors including nitrosoglutathione (GSNO) (FIG. 2A), sodium nitroprusside (SNP), spermine-NO and DETA-NONOate (FIG. 7A). Utilizing the biotin switch method (20), we demonstrate that all four NO donors elicit S-nitrosylation of COX2 in HEK293T cells transfected with COX2-myc (FIG. 2A).

Figure 8A:
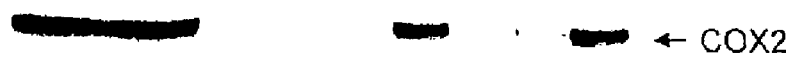
FIG. 8A-8B(S4.) Biotin switch assay is specific for S-nitrosothiol detection.
Figure 8B:

We wondered whether physiological induction of NO formation leads to S-nitrosylation of COX2. In RAW264.7 cells treated with LPS/IFNγ we observe S-nitrosylation of COX2 which is prevented by the iNOS specific inhibitor 1400W using the biotin switch assay (FIG. 2B) as well as the fluorometric method (FIG. 7B). To ensure specificity of the biotin switch method, we have observed that $H_2O_2$ does not elicit S-nitrosylation (FIG. 8A). We ruled out the possibility that sulfenic acid modification is detected by the biotin switch assay by demonstrating that arsenite, which reverses sulfenic acid modifications but not S-nitrosylation, fails to provide the biotin switch signal afforded by ascorbate utilizing GSNO with purified COX2 or LPS/IFNγ treatment of RAW 264.7 cells (FIG. 8B).

Figure 9A:
FIG. 9A-9B. (S5.) Oxyhemoglobin blocks S-nitrosylation of COX2 by exogenous NO but not by endogenous NO produced by iNOS in activated RAW264.7 cells.
Figure 9B:

As NO is freely diffusible, in some instances there may be no need to deliver NO directly to targets, as some actions of NO are prevented by hemoglobin, which can sequester freely diffusible NO(21). We examined the effects of hemoglobin on S-nitrosylation of COX2 under varying conditions. In HEK293T cells transfected with COX2,hemoglobin prevents the S-nitrosylation elicited by GSNO (FIG. 9A) whereas it fails to alter S-nitrosylation of COX2 in RAW264.7 cells activated by LPS/IFNγ (FIG. 9B). Thus in the more physiologic macrophage cell line, the S-nitrosylation of COX2 generated by an inflammatory stimulus does not appear to be elicited by freely diffusible NO.

EXAMPLE 5

S-nitrosylation of COX2 Activates Enzyme Activity

To determine whether S-nitrosylation of COX2 alters enzyme activity, we examined COX2 enzyme activity in HEK293T cells transfected with COX2-myc. The NO donor SNP, added to cell lysates, elicits a substantial augmentation of COX2 activity, which reflects S-nitrosylation, as ascorbic acid, which reverses S-nitrosylation(20, 22), prevents the increase (FIG. 2C and D).

The reversal by ascorbate of COX2 activation by NO donors is not merely a reflection of ascorbate influences on enzymes substrates or intermediate products, as ascorbate fails to affect COX2 activity in preparations not treated by SNP. A relationship of S-nitrosylation and COX2 activation is further supported by the closely similar concentration-response relationship between the effects of the NO donor GSNO on S-nitrosylation and on COX2 activity (FIG. 2E).

NO activates COX2 by increasing its apparent Vmax without changing its Km (FIG. 2E). The higher concentration of SNP required to activate COX2 in vitro compared to intact cells accords with earlier studies showing greater potency of NO donors in intact cells(23, 24). To ascertain the kinetic basis for NO activation of COX2,we conducted enzyme assays with increasing concentrations of sucrose to augment viscosity and slow down enzyme kinetics (FIG. 2G). As expected, with increasing viscosity, the ratio of control enzyme activity to the activity in more viscous solutions increases. This increase is diminished in SNP samples consistent with SNP accelerating the release of product from the enzyme.

EXAMPLE 6

Identification of Cysteine Residue(s) Nitrosylated

Figure 10A:
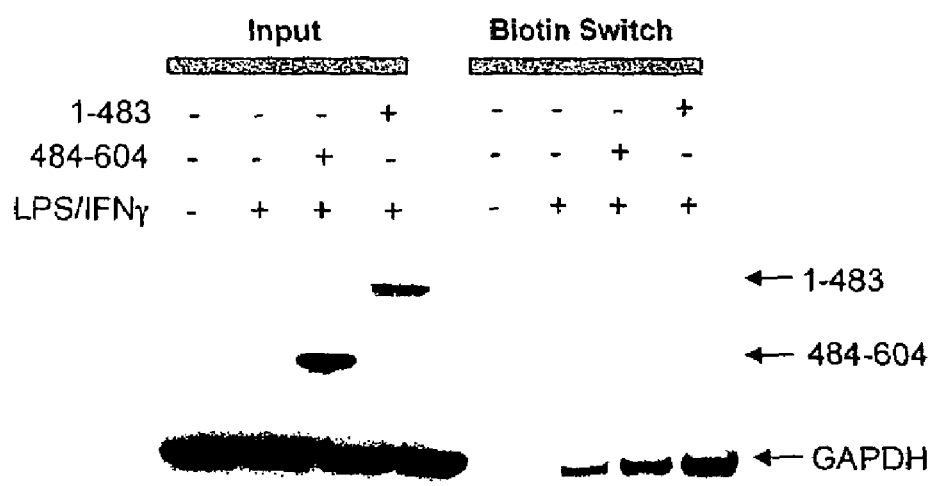
FIG. 10A-10B (S6.) Target of S-nitrosylation of COX2 is located in c-terminus (484-604) and mutation of Cysteine526 to Serine prevents NO-mediated activation of COX2.
Figure 10B:
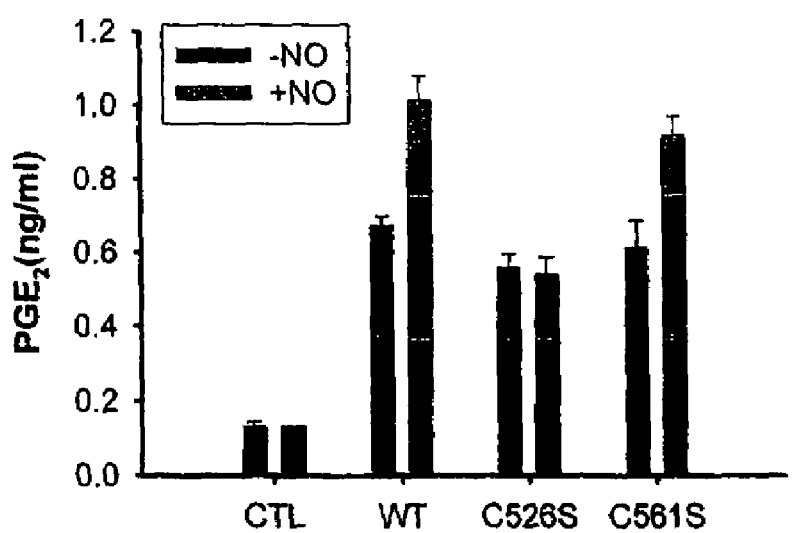

We wondered which of the 13 cysteines of COX2 are critical for the augmentation of COX2 activity elicited by S-nitrosylation. In RAW 264.7 cells transfected with the N-terminal 483 amino acids or the C-terminal 120 amino acids of COX2, LPS/IFNγ treatment leads to S-nitrosylation of the C-terminal fragment (which contains 3 cysteines) but not the N-terminal fragment (FIG. 10A). To ascertain which of these 3 cysteines is responsible for augmented COX2 activity we mutated each of them to serine. The C526S mutation prevents activation of COX2 activity by the NO donor SNP, while the C561S mutation does not (FIG. 10B). The C555S mutation abolishes enzyme activity so the effects of NO stimulation cannot be assessed. Individual mutation of the 13 cysteines in COX2 does not detectably diminish total S-nitrosylation of the enzyme (data not shown), which suggests that multiple cysteines can be S-nitrosylated but only C526 is responsible for enzyme activation by NO.

EXAMPLE 7

The Influence of NO on $PGE_2$ Formation

To clarify the influence of NO on $PGE_2$ formation in a more physiologic preparation, we employed RAW264.7 cells. The formation of $PGE_2$ in response to LPS/IFNγ is inhibited by the iNOS inhibitor 1400W with 50% reduction of $PGE_2$ formation at drug concentrations which provide 50% inhibition of iNOS activity (FIG. 3A). Specificity of the NO association is evident by inhibition of $PGE_2$ formation with the active L-isomer of the NOS inhibitor nitro-argininemethylester (L-NAME) but not by D-NAME; the effects of L-NAME are reversed by added L-arginine (FIG. 3B). Thus, about 50% of induced COX2 activity is determined by S-nitrosylation.

As RAW264.7 cells are a continuous macrophage cell line which may not behave the same as macrophages in intact organisms, we also tested peritoneal macrophages obtained from iNOS knockout mice. $PGE_2$ formation from macrophages of LPS/IFNγ-treated mice is profoundly reduced in the iNOS knockout mice in parallel with a similar reduction in nitrite formation by the macrophages (FIG. 3C) and a decrease in S-nitrosylated COX2 (FIG. 3D). These observations concur with findings of decreased urinary $PGE_2$ in iNOS knockout mice(25).

EXAMPLE 8

Fragment of COX2 (Amino Acids 484-604) Abolishes the Co-precipitation of iNOS and COX2

We hypothesized that the augmentation of $PGE_2$ formation by iNOS activation reflects binding of iNOS to COX2 to deliver NO in appropriate proximity for S-nitrosylation. To explore this possibility we utilized dominant-negative constructs to block iNOS—COX2 binding using the fragment of COX2, amino acids 484-604, which binds iNOS (FIG. 4A). Transfection of 484-604 into RAW264.7 cells abolishes the co-precipitation of iNOS and COX2 and is associated with precipitation of 484-604 together with iNOS (FIG. 4A). Moreover, this interference of binding between COX2 and iNOS by 484-604 decreases S-nitrosylation of COX2 in RAW264.7 cells (FIG. 4B). The dominant-negative transfection also reduces $PGE_2$ formation by more than 50%, whereas transfection of a fragment comprising amino acids 1-483, which does not bind iNOS, fails to influence $PGE_2$ formation (FIGS. 4C and D).

REFERENCES

The disclosure of each reference cited is expressly incorporated herein.

1. M. E. Turini, R. N. DuBois, Annu. Rev. Med. 53, 35 (2002).
2. S. Moncada, J. R. Soc. Med. 92, 164 (1999).
3. R. J. Flower, Nat. Rev. Drug Discov. 2, 179 (2003).
4. D. Mukherjee, S. E. Nissen, E. J. Topol, JAMA 286, 954 (2001).
5. E. J. Topol, JAMA 293, 366 (2005).
6. T. P. Misko, J. L. Trotter, A. H. Cross, J. Neuroimmunol. 61, 195 (1995).
7. I. Appleton, A. Tomlinson, D. A. Willoughby, Adv. Pharmacol. 35, 27 (1996).
8. D. Salvemini et al., J. Clin. Invest 93, 1940 (1994).
9. J. R. Vane, Y. S. Bakhle, R. M. Botting, Annu. Rev. Pharmacol. Toxicol. 38, 97 (1998).
10. D. Salvemini et al., Proc. Natl. Acad. Sci. U.S.A 90, 7240 (1993).
11. J. M. Braughler, C. K. Mittal, F. Murad, J. Biol. Chem. 254, 12450 (1979).
12. J. C. Edwards et al., Biochem. Pharmacol. 30, 2531 (1981).
13. J. S. Stamler, D. J. Singel, J. Loscalzo, Science 258, 1898 (1992).
14. S. R. Jaffrey, H. Erdjument-Bromage, C. D. Ferris, P. Tempst, S. H. Snyder, Nat. Cell Biol. 3, 193 (2001).
15. D. T. Hess, A. Matsumoto, S. O. Kim, H. E. Marshall, J. S. Stamler, Nat. Rev. Mol. Cell Biol. 6, 150 (2005).
16. R. M. Garavito, A. M. Mulichak, Annu. Rev. Biophys. Biomol. Struct. 32, 183 (2003).
17. A. L. Tsai, C. Wei, R. J. Kulmacz, Arch. Biochem. Biophys. 313, 367 (1994).
18. T. A. Kennedy, C. J. Smith, L. J. Marnett, J. Biol. Chem. 269, 27357 (1994).
19. C. J. Smith, L. J. Marnett, Arch. Biochem. Biophys. 335, 342 (1996).
20. S. R. Jaffrey, S. H. Snyder, Sci. STKE. 2001, L1 (2001).
21. F. Murad, C. K. Mittal, W. P. Arnold, S. Katsuki, H. Kimura, Adv. Cyclic. Nucleotide. Res. 9, 145 (1978).
22. Y. Yang, J. Loscalzo, Proc. Natl. Acad. Sci. U.S.A 102, 117 (2005).
23. J. Heo, S. L. Campbell, Biochemistry 43, 2314 (2004).
24. H. M. Lander, J. S. Ogiste, S. F. Pearce, R. Levi, A. Novogrodsky, J. Biol. Chem. 270, 7017 (1995).
25. L. J. Marnett, T. L. Wright, B. C. Crews, S. R. Tannenbaum, J. D. Morrow, J. Biol. Chem. 275, 13427 (2000).
26. D. Salvemini et al., J. Clin. Invest 96, 301 (1995).
27. M. Fang et al., Neuron 28, 183 (2000).
28. H. C. Kornau, L. T. Schenker, M. B. Kennedy, P. H. Seeburg, Science 269, 1737 (1995).
29. R. L. Patterson, D. B. van Rossum, A. I. Kaplin, R. K. Barrow, S. H. Snyder, Proc. Natl. Acad. Sci. U.S.A 102, 1357 (2005).
30. J. Roth, B. Storr, J. Goldbach, K. Voigt, E. Zeisberger, Eur. J. Pharmacol. 383, 177 (1999).
31. H. Guhring et al., J. Neurosci. 20, 6714 (2000).
32. H. Krun, D. Liew, J. Aw, S. Haas, Expert. Rev. Cardiovasc. Ther. 2, 265 (2004).

The invention claimed is:

1. A method of treating inflammation in a patient, comprising:
   administering to the patient a polypeptide consisting of a fragment of human COX2 from the C-terminal 20% of COX2 sufficient to bind iNOS, wherein the fragment comprises a domain of human COX2 which is not present in human COX1, whereby binding of iNOS to COX2 is inhibited in the patient.

2. The method of claim 1 wherein the polypeptide consists of amino acid residues 484-604 of COX2.

* * * * *

UNITED STATES PATENT AND TRADEMARK OFFICE
CERTIFICATE OF CORRECTION

PATENT NO. : 7,358,237 B2  Page 1 of 1
APPLICATION NO. : 11/413201
DATED : April 15, 2008
INVENTOR(S) : Solomon H. Snyder et al.

It is certified that error appears in the above-identified patent and that said Letters Patent is hereby corrected as shown below:

In Columns 69-70, Claim 1, Lines 59-63:
  Please replace "a domain of human COX2 which is not present in human COX1," with --residues 580-597 of human COX2--

Signed and Sealed this

Tenth Day of February, 2009

JOHN DOLL
*Acting Director of the United States Patent and Trademark Office*

SEQUENCE LISTING

<160> NUMBER OF SEQ ID NOS: 14

<210> SEQ ID NO 1
<211> LENGTH: 1153
<212> TYPE: PRT
<213> ORGANISM: Homo sapiens

<400> SEQUENCE: 1

```
Met Ala Cys Pro Trp Lys Phe Leu Phe Lys Thr Lys Phe His Gln Tyr
 1               5                  10                  15

Ala Met Asn Gly Glu Lys Asp Ile Asn Asn Val Glu Lys Ala Pro
            20                  25                  30

Cys Ala Thr Ser Ser Pro Val Thr Gln Asp Asp Leu Gln Tyr His Asn
            35                  40                  45

Leu Ser Lys Gln Gln Asn Glu Ser Pro Gln Pro Leu Val Glu Thr Gly
        50                  55                  60

Lys Lys Ser Pro Glu Ser Leu Val Lys Leu Asp Ala Thr Pro Leu Ser
 65                 70                  75                  80

Ser Pro Arg His Val Arg Ile Lys Asn Trp Gly Ser Gly Met Thr Phe
                    85                  90                  95

Gln Asp Thr Leu His His Lys Ala Lys Gly Ile Leu Thr Cys Arg Ser
                100                 105                 110

Lys Ser Cys Leu Gly Ser Ile Met Thr Pro Lys Ser Leu Thr Arg Gly
            115                 120                 125

Pro Arg Asp Lys Pro Thr Pro Pro Asp Glu Leu Leu Pro Gln Ala Ile
        130                 135                 140

Glu Phe Val Asn Gln Tyr Tyr Gly Ser Phe Lys Glu Ala Lys Ile Glu
145                 150                 155                 160

Glu His Leu Ala Arg Val Glu Ala Val Thr Lys Glu Ile Glu Thr Thr
                165                 170                 175

Gly Thr Tyr Gln Leu Thr Gly Asp Glu Leu Ile Phe Ala Thr Lys Gln
                180                 185                 190

Ala Trp Arg Asn Ala Pro Arg Cys Ile Gly Arg Ile Gln Trp Ser Asn
            195                 200                 205

Leu Gln Val Phe Asp Ala Arg Ser Cys Ser Thr Ala Arg Glu Met Phe
        210                 215                 220

Glu His Ile Cys Arg His Val Arg Tyr Ser Thr Asn Asn Gly Asn Ile
225                 230                 235                 240

Arg Ser Ala Ile Thr Val Phe Pro Gln Arg Ser Asp Gly Lys His Asp
                245                 250                 255

Phe Arg Val Trp Asn Ala Gln Leu Ile Arg Tyr Ala Gly Tyr Gln Met
                260                 265                 270

Pro Asp Gly Ser Ile Arg Gly Asp Pro Ala Asn Val Glu Phe Thr Gln
            275                 280                 285

Leu Cys Ile Asp Leu Gly Trp Lys Pro Lys Tyr Gly Arg Phe Asp Val
        290                 295                 300

Val Pro Leu Val Leu Gln Ala Asn Gly Arg Asp Pro Glu Leu Phe Glu
305                 310                 315                 320

Ile Pro Pro Asp Leu Val Leu Glu Val Ala Met Glu His Pro Lys Tyr
                325                 330                 335

Glu Trp Phe Arg Glu Leu Glu Leu Lys Trp Tyr Ala Leu Pro Ala Val
                340                 345                 350

Ala Asn Met Leu Leu Glu Val Gly Gly Leu Glu Phe Pro Gly Cys Pro
```

-continued

```
            355                 360                 365
Phe Asn Gly Trp Tyr Met Gly Thr Glu Ile Gly Val Arg Asp Phe Cys
    370                 375                 380

Asp Val Gln Arg Tyr Asn Ile Leu Glu Val Gly Arg Arg Met Gly
385                 390                 395                 400

Leu Glu Thr His Lys Leu Ala Ser Leu Trp Lys Asp Gln Ala Val Val
                    405                 410                 415

Glu Ile Asn Ile Ala Val Leu His Ser Phe Gln Lys Gln Asn Val Thr
                420                 425                 430

Ile Met Asp His His Ser Ala Ala Glu Ser Phe Met Lys Tyr Met Gln
            435                 440                 445

Asn Glu Tyr Arg Ser Arg Gly Gly Cys Pro Ala Asp Trp Ile Trp Leu
450                 455                 460

Val Pro Pro Met Ser Gly Ser Ile Thr Pro Val Phe His Gln Glu Met
465                 470                 475                 480

Leu Asn Tyr Val Leu Ser Pro Phe Tyr Tyr Gln Val Glu Ala Trp
                485                 490                 495

Lys Thr His Val Trp Gln Asp Glu Lys Arg Arg Pro Lys Arg Arg Glu
            500                 505                 510

Ile Pro Leu Lys Val Leu Val Lys Ala Val Leu Phe Ala Cys Met Leu
        515                 520                 525

Met Arg Lys Thr Met Ala Ser Arg Val Arg Val Thr Ile Leu Phe Ala
    530                 535                 540

Thr Glu Thr Gly Lys Ser Glu Ala Leu Ala Trp Asp Leu Gly Ala Leu
545                 550                 555                 560

Phe Ser Cys Ala Phe Asn Pro Lys Val Val Cys Met Asp Lys Tyr Arg
                565                 570                 575

Leu Ser Cys Leu Glu Glu Arg Leu Leu Leu Val Val Thr Ser Thr
                580                 585                 590

Phe Gly Asn Gly Asp Cys Pro Gly Asn Gly Glu Lys Leu Lys Lys Ser
                595                 600                 605

Leu Phe Met Leu Lys Glu Leu Asn Asn Lys Phe Arg Tyr Ala Val Phe
    610                 615                 620

Gly Leu Gly Ser Ser Met Tyr Pro Arg Phe Cys Ala Phe Ala His Asp
625                 630                 635                 640

Ile Asp Gln Lys Leu Ser His Leu Gly Ala Ser Gln Leu Thr Pro Met
                645                 650                 655

Gly Glu Gly Asp Glu Leu Ser Gly Gln Glu Asp Ala Phe Arg Ser Trp
                660                 665                 670

Ala Val Gln Thr Phe Lys Ala Ala Cys Glu Thr Phe Asp Val Arg Gly
            675                 680                 685

Lys Gln His Ile Gln Ile Pro Lys Leu Tyr Thr Ser Asn Val Thr Trp
    690                 695                 700

Asp Pro His His Tyr Arg Leu Val Gln Asp Ser Gln Pro Leu Asp Leu
705                 710                 715                 720

Ser Lys Ala Leu Ser Ser Met His Ala Lys Asn Val Phe Thr Met Arg
                725                 730                 735

Leu Lys Ser Arg Gln Asn Leu Gln Ser Pro Thr Ser Ser Arg Ala Thr
                740                 745                 750

Ile Leu Val Glu Leu Ser Cys Glu Asp Gly Gln Gly Leu Asn Tyr Leu
            755                 760                 765

Pro Gly Glu His Leu Gly Val Cys Pro Gly Asn Gln Pro Ala Leu Val
770                 775                 780
```

```
Gln Gly Ile Leu Glu Arg Val Val Asp Gly Thr Pro His Gln Thr
785                 790                 795                 800

Val Arg Leu Glu Ala Leu Asp Glu Ser Gly Ser Tyr Trp Val Ser Asp
            805                 810                 815

Lys Arg Leu Pro Pro Cys Ser Leu Ser Gln Ala Leu Thr Tyr Phe Leu
            820                 825                 830

Asp Ile Thr Thr Pro Pro Thr Gln Leu Leu Leu Gln Lys Leu Ala Gln
            835                 840                 845

Val Ala Thr Glu Glu Pro Glu Arg Gln Arg Leu Glu Ala Leu Cys Gln
850                 855                 860

Pro Ser Glu Tyr Ser Lys Trp Lys Phe Thr Asn Ser Pro Thr Phe Leu
865                 870                 875                 880

Glu Val Leu Glu Glu Phe Pro Ser Leu Arg Val Ser Ala Gly Phe Leu
                885                 890                 895

Leu Ser Gln Leu Pro Ile Leu Lys Pro Arg Phe Tyr Ser Ile Ser Ser
                900                 905                 910

Ser Arg Asp His Thr Pro Thr Glu Ile His Leu Thr Val Ala Val Val
            915                 920                 925

Thr Tyr His Thr Arg Asp Gly Gln Gly Pro Leu His His Gly Val Cys
930                 935                 940

Ser Thr Trp Leu Asn Ser Leu Lys Pro Gln Asp Pro Val Pro Cys Phe
945                 950                 955                 960

Val Arg Asn Ala Ser Gly Phe His Leu Pro Glu Asp Pro Ser His Pro
                965                 970                 975

Cys Ile Leu Ile Gly Pro Gly Thr Gly Ile Ala Pro Phe Arg Ser Phe
            980                 985                 990

Trp Gln Gln Arg Leu His Asp Ser Gln His Lys Gly Val Arg Gly Gly
                995                 1000                1005

Arg Met Thr Leu Val Phe Gly Cys Arg Arg Pro Asp Glu Asp His Ile
        1010                1015                1020

Tyr Gln Glu Glu Met Leu Glu Met Ala Gln Lys Gly Val Leu His Ala
1025                1030                1035                1040

Val His Thr Ala Tyr Ser Arg Leu Pro Gly Lys Pro Lys Val Tyr Val
                1045                1050                1055

Gln Asp Ile Leu Arg Gln Gln Leu Ala Ser Glu Val Leu Arg Val Leu
            1060                1065                1070

His Lys Glu Pro Gly His Leu Tyr Val Cys Gly Asp Val Arg Met Ala
        1075                1080                1085

Arg Asp Val Ala His Thr Leu Lys Gln Leu Val Ala Ala Lys Leu Lys
        1090                1095                1100

Leu Asn Glu Glu Gln Val Glu Asp Tyr Phe Phe Gln Leu Lys Ser Gln
1105                1110                1115                1120

Lys Arg Tyr His Glu Asp Ile Phe Gly Ala Val Phe Pro Tyr Glu Ala
            1125                1130                1135

Lys Lys Asp Arg Val Ala Val Gln Pro Ser Ser Leu Glu Met Ser Ala
            1140                1145                1150

Leu

<210> SEQ ID NO 2
<211> LENGTH: 604
<212> TYPE: PRT
<213> ORGANISM: Homo sapiens

<400> SEQUENCE: 2
```

-continued

```
Met Leu Ala Arg Ala Leu Leu Leu Cys Ala Val Leu Ala Leu Ser His
 1               5                  10                  15

Thr Ala Asn Pro Cys Cys Ser His Pro Cys Gln Asn Arg Gly Val Cys
             20                  25                  30

Met Ser Val Gly Phe Asp Gln Tyr Lys Cys Asp Cys Thr Arg Thr Gly
         35                  40                  45

Phe Tyr Gly Glu Asn Cys Ser Thr Pro Glu Phe Leu Thr Arg Ile Lys
     50                  55                  60

Leu Phe Leu Lys Pro Thr Pro Asn Thr Val His Tyr Ile Leu Thr His
 65                  70                  75                  80

Phe Lys Gly Phe Trp Asn Val Val Asn Asn Ile Pro Phe Leu Arg Asn
                 85                  90                  95

Ala Ile Met Ser Tyr Val Leu Thr Ser Arg Ser His Leu Ile Asp Ser
             100                 105                 110

Pro Pro Thr Tyr Asn Ala Asp Tyr Gly Tyr Lys Ser Trp Glu Ala Phe
         115                 120                 125

Ser Asn Leu Ser Tyr Tyr Thr Arg Ala Leu Pro Pro Val Pro Asp Asp
     130                 135                 140

Cys Pro Thr Pro Leu Gly Val Lys Gly Lys Lys Gln Leu Pro Asp Ser
145                 150                 155                 160

Asn Glu Ile Val Glu Lys Leu Leu Leu Arg Arg Lys Phe Ile Pro Asp
                 165                 170                 175

Pro Gln Gly Ser Asn Met Met Phe Ala Phe Phe Ala Gln His Phe Thr
             180                 185                 190

His Gln Phe Phe Lys Thr Asp His Lys Arg Gly Pro Ala Phe Thr Asn
         195                 200                 205

Gly Leu Gly His Gly Val Asp Leu Asn His Ile Tyr Gly Glu Thr Leu
     210                 215                 220

Ala Arg Gln Arg Lys Leu Arg Leu Phe Lys Asp Gly Lys Met Lys Tyr
225                 230                 235                 240

Gln Ile Ile Asp Gly Glu Met Tyr Pro Pro Thr Val Lys Asp Thr Gln
                 245                 250                 255

Ala Glu Met Ile Tyr Pro Pro Gln Val Pro Glu His Leu Arg Phe Ala
             260                 265                 270

Val Gly Gln Glu Val Phe Gly Leu Val Pro Gly Leu Met Met Tyr Ala
         275                 280                 285

Thr Ile Trp Leu Arg Glu His Asn Arg Val Cys Asp Val Leu Lys Gln
     290                 295                 300

Glu His Pro Glu Trp Gly Asp Glu Gln Leu Phe Gln Thr Ser Arg Leu
305                 310                 315                 320

Ile Leu Ile Gly Glu Thr Ile Lys Ile Val Ile Glu Asp Tyr Val Gln
                 325                 330                 335

His Leu Ser Gly Tyr His Phe Lys Leu Lys Phe Asp Pro Glu Leu Leu
             340                 345                 350

Phe Asn Lys Gln Phe Gln Tyr Gln Asn Arg Ile Ala Ala Glu Phe Asn
         355                 360                 365

Thr Leu Tyr His Trp His Pro Leu Leu Pro Asp Thr Phe Gln Ile His
     370                 375                 380

Asp Gln Lys Tyr Asn Tyr Gln Gln Phe Ile Tyr Asn Asn Ser Ile Leu
385                 390                 395                 400

Leu Glu His Gly Ile Thr Gln Phe Val Glu Ser Phe Thr Arg Gln Ile
                 405                 410                 415
```

```
Ala Gly Arg Val Ala Gly Gly Arg Asn Val Pro Pro Ala Val Gln Lys
            420                 425                 430

Val Ser Gln Ala Ser Ile Asp Gln Ser Arg Gln Met Lys Tyr Gln Ser
        435                 440                 445

Phe Asn Glu Tyr Arg Lys Arg Phe Met Leu Lys Pro Tyr Glu Ser Phe
    450                 455                 460

Glu Glu Leu Thr Gly Glu Lys Glu Met Ser Ala Glu Leu Glu Ala Leu
465                 470                 475                 480

Tyr Gly Asp Ile Asp Ala Val Glu Leu Tyr Pro Ala Leu Leu Val Glu
                485                 490                 495

Lys Pro Arg Pro Asp Ala Ile Phe Gly Glu Thr Met Val Glu Val Gly
            500                 505                 510

Ala Pro Phe Ser Leu Lys Gly Leu Met Gly Asn Val Ile Cys Ser Pro
        515                 520                 525

Ala Tyr Trp Lys Pro Ser Thr Phe Gly Gly Glu Val Gly Phe Gln Ile
    530                 535                 540

Ile Asn Thr Ala Ser Ile Gln Ser Leu Ile Cys Asn Asn Val Lys Gly
545                 550                 555                 560

Cys Pro Phe Thr Ser Phe Ser Val Pro Asp Pro Glu Leu Ile Lys Thr
                565                 570                 575

Val Thr Ile Asn Ala Ser Ser Ser Arg Ser Gly Leu Asp Asp Ile Asn
            580                 585                 590

Pro Thr Val Leu Leu Lys Glu Arg Ser Thr Glu Leu
        595                 600

<210> SEQ ID NO 3
<211> LENGTH: 1154
<212> TYPE: PRT
<213> ORGANISM: Canis familiaris

<400> SEQUENCE: 3

Met Ala Cys Pro Trp Lys Phe Leu Phe Arg Ala Lys Phe His Gln Tyr
  1               5                  10                  15

Gly Met Lys Glu Glu Lys Asp Ile Asn Asn Asn Val Glu Lys Pro Pro
            20                  25                  30

Gly Ala Thr Pro Ser Pro Ser Thr Gln Asp Asp Leu Lys Asn His Lys
        35                  40                  45

His His Asn Asp Ser Pro Gln Pro Leu Thr Glu Thr Val Gln Lys Leu
    50                  55                  60

Pro Glu Ser Leu Asp Lys Leu His Ala Thr Pro Leu Ser Arg Pro Gln
65                  70                  75                  80

His Val Arg Ile Lys Asn Trp Gly Asn Gly Arg Ser Phe Gln Asp Thr
                85                  90                  95

Leu His His Lys Ala Met Gly Val Leu Ala Cys Thr Ser Lys Leu Cys
            100                 105                 110

Met Gly Ser Ile Met Asn Thr Lys Ser Leu Thr Arg Gly Pro Ser Asp
        115                 120                 125

Lys Pro Thr Pro Thr Glu Glu Leu Leu Pro Gln Ala Ile Glu Phe Val
    130                 135                 140

Asn Gln Tyr Tyr Gly Ser Phe Lys Glu Ala Lys Ile Glu Glu His Leu
145                 150                 155                 160

Ala Arg Val Glu Ala Val Thr Lys Asp Ile Glu Thr Gly Thr Tyr
                165                 170                 175

Gln Leu Thr Gly Asp Glu Leu Ile Phe Ala Thr Lys Gln Ala Trp Arg
            180                 185                 190
```

```
Asn Ala Pro Arg Cys Ile Gly Arg Ile Gln Trp Ser Asn Leu Gln Val
            195                 200                 205

Phe Asp Ala Arg Ser Cys Ser Thr Ala Lys Glu Met Phe Glu His Ile
            210                 215                 220

Cys Arg His Leu Arg Tyr Ala Ser Asn Asn Gly Asn Ile Arg Ser Ala
225                 230                 235                 240

Ile Thr Val Phe Pro Gln Arg Thr Asp Gly Lys His Asp Phe Arg Val
            245                 250                 255

Trp Asn Ala Gln Leu Ile Arg Tyr Ala Gly Tyr Gln Met Pro Asp Gly
            260                 265                 270

Thr Ile Leu Gly Asp Pro Ala Ser Val Glu Phe Thr Gln Leu Cys Ile
            275                 280                 285

Asp Leu Gly Trp Lys Pro Lys Tyr Gly Arg Phe Asp Val Val Pro Leu
            290                 295                 300

Val Leu Gln Ala Asp Gly Gln Asp Pro Glu Phe Phe Glu Ile Pro Pro
305                 310                 315                 320

Asp Leu Val Leu Glu Val Pro Met Glu His Pro Lys Tyr Glu Trp Phe
            325                 330                 335

Arg Glu Leu Glu Leu Lys Trp Tyr Ala Leu Pro Ala Val Ala Asn Met
            340                 345                 350

Leu Leu Glu Val Gly Gly Leu Glu Phe Pro Gly Cys Pro Phe Asn Gly
            355                 360                 365

Trp Tyr Met Gly Thr Glu Ile Gly Val Arg Asp Phe Cys Asp Val Gln
            370                 375                 380

Arg Tyr Asn Ile Leu Glu Glu Val Gly Ser Lys Met Gly Leu Glu Thr
385                 390                 395                 400

His Lys Leu Ala Ser Leu Trp Lys Asp Arg Ala Val Ile Glu Ile Asn
                405                 410                 415

Val Ala Val Leu His Ser Phe Gln Lys Gln Asn Val Thr Ile Met Asp
            420                 425                 430

His His Ser Ala Ala Glu Ser Phe Met Lys Tyr Met Gln Ser Glu Tyr
            435                 440                 445

Arg Ser Arg Gly Gly Cys Pro Ala Asp Trp Ile Trp Leu Val Pro Pro
450                 455                 460

Ile Ser Gly Ser Ile Thr Pro Val Phe His Gln Glu Met Leu Asn Tyr
465                 470                 475                 480

Val Leu Ser Pro Phe Tyr Tyr Tyr Gln Val Glu Ala Trp Lys Thr His
            485                 490                 495

Leu Trp Leu Asp Glu Lys Arg Arg Pro His Arg Lys Lys Ile Gln Leu
            500                 505                 510

Lys Val Leu Val Lys Ala Val Leu Phe Ala Ser Met Leu Met Arg Lys
            515                 520                 525

Thr Met Ala Ser Arg Val Arg Val Thr Ile Leu Phe Ala Thr Glu Thr
            530                 535                 540

Gly Lys Ser Glu Thr Leu Ala Arg Asp Leu Gly Ala Leu Phe Ser Cys
545                 550                 555                 560

Ala Phe His Pro Lys Val Leu Cys Met Asp Glu Tyr Lys Leu Ser His
            565                 570                 575

Leu Glu Glu Glu Gln Leu Leu Leu Val Val Thr Ser Thr Phe Gly Asn
            580                 585                 590

Gly Asp Ser Pro Gly Asn Gly Glu Lys Leu Lys Lys Ser Leu Phe Met
            595                 600                 605
```

```
Leu Lys Glu Leu Thr Asn Asn Phe Arg Tyr Ala Val Phe Gly Leu Arg
    610                 615                 620

Ser Asn Met Tyr Pro Gln Phe Cys Ala Phe Ala His Asp Ile Asp His
625                 630                 635                 640

Lys Leu Ser His Leu Gly Ala Ser Gln Leu Thr Pro Gly Gly Glu Gly
                645                 650                 655

Asp Glu Leu Asn Gly Lys Glu Glu Ala Phe Arg Cys Trp Ala Val Gln
                660                 665                 670

Thr Phe Lys Ala Ala Cys Asp Thr Ser Asp Val Arg Gly Lys His Cys
                675                 680                 685

Ile Gln Ile Pro Arg Leu Tyr Thr Ser Asn Val Thr Trp Asp Pro His
    690                 695                 700

His Tyr Arg Leu Leu Gln Asp Ser Gln Pro Leu Asp Leu Asn Lys Ala
705                 710                 715                 720

Leu Ser Lys Met His Ala Lys Asn Val Phe Thr Leu Arg Leu Lys Ser
                725                 730                 735

Gln Arg Asn Leu Gln Ser Pro Ile Ser Asn Arg Thr Thr Leu Gln Val
                740                 745                 750

Glu Leu Ser Cys Glu Asp Ser Gln Glu Leu Ser Tyr Leu Pro Gly Glu
                755                 760                 765

His Leu Gly Val Phe Pro Gly Asn Gln Leu Ala Leu Val Gln Gly Ile
    770                 775                 780

Leu Glu Arg Val Val Tyr Ser Pro Ala Pro Leu Gln Pro Val His Leu
785                 790                 795                 800

Glu Thr Leu Ser Glu Arg Gly Ser Tyr Trp Val Arg Asn Asn Arg Leu
                805                 810                 815

Pro Pro Cys Ser Leu Ser Gln Ala Leu Thr Tyr Phe Leu Asp Ile Thr
                820                 825                 830

Thr Pro Pro Thr His Leu Leu Leu Arg Lys Leu Ala Gln Leu Ala His
                835                 840                 845

Gln Tyr Ala Glu Arg His Arg Leu Glu Ile Leu Cys His Pro Ser Glu
    850                 855                 860

Tyr Asn Lys Trp Lys Leu Thr Asn Ser Pro Thr Phe Leu Glu Val Leu
865                 870                 875                 880

Glu Glu Phe Pro Ser Leu Arg Val Ser Ala Gly Phe Leu Leu Ser Gln
                885                 890                 895

Leu Pro Ile Leu Lys Pro Arg Tyr Tyr Ser Ile Ser Ser Ser Arg Asp
                900                 905                 910

Cys Thr Pro Met Glu Val His Leu Thr Val Ala Val Leu Val Tyr Pro
    915                 920                 925

Thr Arg Asp Gly Gln Gly Pro Leu His His Gly Val Cys Ser Thr Trp
    930                 935                 940

Leu Ser Asn Leu Lys Pro Gln Asp Pro Val Pro Cys Phe Val Arg Ser
945                 950                 955                 960

Ala Gly Asn Phe Lys Leu Pro Glu Asp Pro Ser Arg Pro Cys Ile Leu
                965                 970                 975

Ile Gly Pro Gly Thr Gly Ile Ala Pro Phe Arg Ser Phe Trp Gln Gln
                980                 985                 990

Arg Leu His Asp Ile Lys His Lys Gly Leu Arg Gly Ser Arg Met Thr
                995                 1000                1005

Leu Val Phe Gly Cys Arg Arg Pro Asp Glu Asp His Leu Tyr Arg Glu
    1010                1015                1020

Glu Met Leu Glu Met Ala Gln Ser Gly Val Leu His Glu Val His Thr
```

-continued

```
                1025                1030                1035                1040
Ala Tyr Ser Arg Leu Pro Gly Gln Pro Lys Val Tyr Val Gln Asp Ile
            1045                1050                1055

Leu Arg Gln Gln Leu Ala Ser Gln Val Leu Arg Met Leu His Glu Glu
        1060                1065                1070

Gln Gly His Leu Tyr Val Cys Gly Asp Val Arg Met Ala Arg Asp Val
        1075                1080                1085

Ala His Thr Leu Lys His Leu Val Ala Ala Lys Leu Ser Leu Ser Glu
        1090                1095                1100

Glu Gln Val Glu Asp Tyr Phe Phe Gln Leu Lys Ser Gln Lys Arg Tyr
1105                1110                1115                1120

His Glu Asp Ile Phe Gly Ala Val Phe Pro Tyr Glu Val Lys Lys Asp
                1125                1130                1135

Gly Ala Ala Lys Gln Pro Ser Asp Pro Arg Val Pro Ala Ala His Gly
            1140                1145                1150

Arg Ser

<210> SEQ ID NO 4
<211> LENGTH: 1144
<212> TYPE: PRT
<213> ORGANISM: Mus musculus

<400> SEQUENCE: 4

Met Ala Cys Pro Trp Lys Phe Leu Phe Lys Val Lys Ser Tyr Gln Ser
1               5                   10                  15

Asp Leu Lys Glu Glu Lys Asp Ile Asn Asn Asn Val Lys Lys Thr Pro
            20                  25                  30

Cys Ala Val Leu Ser Pro Thr Ile Gln Asp Asp Pro Lys Ser His Gln
        35                  40                  45

Asn Gly Ser Pro Gln Leu Leu Thr Gly Thr Ala Gln Asn Val Pro Glu
    50                  55                  60

Ser Leu Asp Lys Leu His Val Thr Ser Thr Arg Pro Gln Tyr Val Arg
65                  70                  75                  80

Ile Lys Asn Trp Gly Ser Gly Glu Ile Leu His Asp Thr Leu His His
                85                  90                  95

Lys Ala Thr Ser Asp Phe Thr Cys Lys Ser Lys Ser Cys Leu Gly Ser
            100                 105                 110

Ile Met Asn Pro Lys Ser Leu Thr Arg Gly Pro Arg Asp Lys Pro Thr
        115                 120                 125

Pro Leu Glu Glu Leu Leu Pro His Ala Ile Glu Phe Ile Asn Gln Tyr
    130                 135                 140

Tyr Gly Ser Phe Lys Glu Ala Lys Ile Glu Glu His Leu Ala Arg Leu
145                 150                 155                 160

Glu Ala Val Thr Lys Glu Ile Glu Thr Thr Gly Thr Tyr Gln Leu Thr
                165                 170                 175

Leu Asp Glu Leu Ile Phe Ala Thr Lys Met Ala Trp Arg Asn Ala Pro
            180                 185                 190

Arg Cys Ile Gly Arg Ile Gln Trp Ser Asn Leu Gln Val Phe Asp Ala
        195                 200                 205

Arg Asn Cys Ser Thr Ala Gln Glu Met Phe Gln His Ile Cys Arg His
    210                 215                 220

Ile Leu Tyr Ala Thr Asn Asn Gly Asn Ile Arg Ser Ala Ile Thr Val
225                 230                 235                 240

Phe Pro Gln Arg Ser Asp Gly Lys His Asp Phe Arg Leu Trp Asn Ser
```

-continued

```
                245                 250                 255
Gln Leu Ile Arg Tyr Ala Gly Tyr Gln Met Pro Asp Gly Thr Ile Arg
            260                 265                 270
Gly Asp Ala Ala Thr Leu Glu Phe Thr Gln Leu Cys Ile Asp Leu Gly
            275                 280                 285
Trp Lys Pro Arg Tyr Gly Arg Phe Asp Val Leu Pro Leu Val Leu Gln
            290                 295                 300
Ala Asp Gly Gln Asp Pro Glu Val Phe Glu Ile Pro Pro Asp Leu Val
305                 310                 315                 320
Leu Glu Val Thr Met Glu His Pro Lys Tyr Glu Trp Phe Gln Glu Leu
                325                 330                 335
Gly Leu Lys Trp Tyr Ala Leu Pro Ala Val Ala Asn Met Leu Leu Glu
            340                 345                 350
Val Gly Gly Leu Glu Phe Pro Ala Cys Pro Phe Asn Gly Trp Tyr Met
            355                 360                 365
Gly Thr Glu Ile Gly Val Arg Asp Phe Cys Asp Thr Gln Arg Tyr Asn
            370                 375                 380
Ile Leu Glu Glu Val Gly Arg Arg Met Gly Leu Glu Thr His Thr Leu
385                 390                 395                 400
Ala Ser Leu Trp Lys Asp Arg Ala Val Thr Glu Ile Asn Val Ala Val
                405                 410                 415
Leu His Ser Phe Gln Lys Gln Asn Val Thr Ile Met Asp His His Thr
            420                 425                 430
Ala Ser Glu Ser Phe Met Lys His Met Gln Asn Glu Tyr Arg Ala Arg
            435                 440                 445
Gly Gly Cys Pro Ala Asp Trp Ile Trp Leu Val Pro Pro Val Ser Gly
            450                 455                 460
Ser Ile Thr Pro Val Phe His Gln Glu Met Leu Asn Tyr Val Leu Ser
465                 470                 475                 480
Pro Phe Tyr Tyr Tyr Gln Ile Glu Pro Trp Lys Thr His Ile Trp Gln
                485                 490                 495
Asn Glu Lys Leu Arg Pro Arg Arg Glu Ile Arg Phe Arg Val Leu
            500                 505                 510
Val Lys Val Val Phe Phe Ala Ser Met Leu Met Arg Lys Val Met Ala
            515                 520                 525
Ser Arg Val Arg Ala Thr Val Leu Phe Ala Thr Glu Thr Gly Lys Ser
            530                 535                 540
Glu Ala Leu Ala Arg Asp Leu Ala Thr Leu Phe Ser Tyr Ala Phe Asn
545                 550                 555                 560
Thr Lys Val Val Cys Met Asp Gln Tyr Lys Ala Ser Thr Leu Glu Glu
                565                 570                 575
Glu Gln Leu Leu Leu Val Val Thr Ser Thr Phe Gly Asn Gly Asp Cys
            580                 585                 590
Pro Ser Asn Gly Gln Thr Leu Lys Lys Ser Leu Phe Met Leu Arg Glu
            595                 600                 605
Leu Asn His Thr Phe Arg Tyr Ala Val Phe Gly Leu Gly Ser Ser Met
            610                 615                 620
Tyr Pro Gln Phe Cys Ala Phe Ala His Asp Ile Asp Gln Lys Leu Ser
625                 630                 635                 640
His Leu Gly Ala Ser Gln Leu Ala Pro Thr Gly Glu Gly Asp Glu Leu
                645                 650                 655
Ser Gly Gln Glu Asp Ala Phe Arg Ser Trp Ala Val Gln Thr Phe Arg
            660                 665                 670
```

-continued

```
Ala Ala Cys Glu Thr Phe Asp Val Arg Ser Lys His His Ile Gln Ile
        675                 680                 685

Pro Lys Arg Phe Thr Ser Asn Ala Thr Trp Glu Pro Gln Gln Tyr Arg
690                 695                 700

Leu Ile Gln Ser Pro Glu Pro Leu Asp Leu Asn Arg Ala Leu Ser Ser
705                 710                 715                 720

Ile His Ala Lys Asn Val Phe Thr Met Arg Leu Lys Ser Gln Gln Asn
                725                 730                 735

Leu Gln Ser Glu Lys Ser Ser Arg Thr Thr Leu Leu Val Gln Leu Thr
            740                 745                 750

Phe Glu Gly Ser Arg Gly Pro Ser Tyr Leu Pro Gly Glu His Leu Gly
        755                 760                 765

Ile Phe Pro Gly Asn Gln Thr Ala Leu Val Gln Gly Ile Leu Glu Arg
    770                 775                 780

Val Val Asp Cys Pro Thr Pro His Gln Thr Val Cys Leu Glu Val Leu
785                 790                 795                 800

Asp Glu Ser Gly Ser Tyr Trp Val Lys Asp Lys Arg Leu Pro Pro Cys
                805                 810                 815

Ser Leu Ser Gln Ala Leu Thr Tyr Phe Leu Asp Ile Thr Thr Pro Pro
            820                 825                 830

Thr Gln Leu Gln Leu His Lys Leu Ala Arg Phe Ala Thr Asp Glu Thr
        835                 840                 845

Asp Arg Gln Arg Leu Glu Ala Leu Cys Gln Pro Ser Glu Tyr Asn Asp
    850                 855                 860

Trp Lys Phe Ser Asn Asn Pro Thr Phe Leu Glu Val Leu Glu Glu Phe
865                 870                 875                 880

Pro Ser Leu His Val Pro Ala Ala Phe Leu Leu Ser Gln Leu Pro Ile
                885                 890                 895

Leu Lys Pro Arg Tyr Tyr Ser Ile Ser Ser Ser Gln Asp His Thr Pro
            900                 905                 910

Ser Glu Val His Leu Thr Val Ala Val Val Thr Tyr Arg Thr Arg Asp
        915                 920                 925

Gly Gln Gly Pro Leu His His Gly Val Cys Ser Thr Trp Ile Arg Asn
    930                 935                 940

Leu Lys Pro Gln Asp Pro Val Pro Cys Phe Val Arg Ser Val Ser Gly
945                 950                 955                 960

Phe Gln Leu Pro Glu Asp Pro Ser Gln Pro Cys Ile Leu Ile Gly Pro
                965                 970                 975

Gly Thr Gly Ile Ala Pro Phe Arg Ser Phe Trp Gln Arg Leu His
            980                 985                 990

Asp Ser Gln His Lys Gly Leu Lys Gly Gly Arg Met Ser Leu Val Phe
        995                 1000                1005

Gly Cys Arg His Pro Glu Glu Asp His Leu Tyr Gln Glu Glu Met Gln
    1010                1015                1020

Glu Met Val Arg Lys Arg Val Leu Phe Gln Val His Thr Gly Tyr Ser
1025                1030                1035                1040

Arg Leu Pro Gly Lys Pro Lys Val Tyr Val Gln Asp Ile Leu Gln Lys
                1045                1050                1055

Gln Leu Ala Asn Glu Val Leu Ser Val Leu His Gly Glu Gln Gly His
            1060                1065                1070

Leu Tyr Ile Cys Gly Asp Val Arg Met Ala Arg Asp Val Ala Thr Thr
        1075                1080                1085
```

```
Leu Lys Lys Leu Val Ala Thr Lys Leu Asn Leu Ser Glu Glu Gln Val
    1090                1095                1100

Glu Asp Tyr Phe Phe Gln Leu Lys Ser Gln Lys Arg Tyr His Glu Asp
1105                1110                1115                1120

Ile Phe Gly Ala Val Phe Ser Tyr Gly Ala Lys Lys Gly Ser Ala Leu
                1125                1130                1135

Glu Glu Pro Lys Ala Thr Arg Leu
            1140

<210> SEQ ID NO 5
<211> LENGTH: 1136
<212> TYPE: PRT
<213> ORGANISM: Gallus gallus

<400> SEQUENCE: 5

Met Leu Cys Pro Trp Gln Phe Ala Phe Lys Pro His Ala Val Lys Asn
1               5                   10                  15

Gln Ser Ser Glu Glu Lys Asp Ile Asn Asn Val Glu Lys Asp Val
            20                  25                  30

Lys Val His Ser Phe Val Lys Asp Ala Lys Leu His Ser Leu Ser
                35                  40                  45

Lys Lys Gln Met Lys Met Ser Pro Ile Ile Thr Ser Ala Glu Lys His
    50                  55                  60

Pro Gln Asn Gly Ile Lys Ala Ser Asn Gln Ile Ser Arg Cys Pro Arg
65                  70                  75                  80

His Val Lys Val Arg Asn Met Glu Asn Gly Ser Ser Leu Leu Asp Thr
                85                  90                  95

Leu His Leu Thr Ala Lys Glu Val Ile Asn Cys Arg Thr Arg Ala Cys
            100                 105                 110

Gln Gly Ala Leu Met Thr Pro Lys Gly Leu Val Arg Ser Thr Arg Asp
        115                 120                 125

Gly Pro Val Pro Pro Ala Glu Leu Leu Pro Gln Ala Val Asp Phe Val
    130                 135                 140

Lys Gln Tyr Tyr Ser Ser Phe Lys Glu Leu Lys Ile Glu Glu His Leu
145                 150                 155                 160

Ala Arg Leu Glu Thr Val Thr Lys Glu Ile Glu Thr Thr Gly Thr Tyr
                165                 170                 175

His Leu Thr Lys Asp Glu Leu Ile Phe Ala Ala Lys Gln Ala Trp Arg
            180                 185                 190

Asn Ala Pro Arg Cys Ile Gly Arg Ile Gln Trp Ser Asn Leu Gln Val
        195                 200                 205

Phe Asp Ala Arg Asp Cys Lys Thr Ala Lys Glu Met Phe Glu Tyr Ile
    210                 215                 220

Cys Arg His Ile Gln Tyr Ala Thr Asn Asn Gly Asn Ile Arg Ser Ala
225                 230                 235                 240

Ile Thr Ile Phe Pro Gln Arg Thr Asp Gly Lys His Asp Phe Arg Val
                245                 250                 255

Trp Asn Ser Gln Leu Ile Arg Tyr Ala Gly Tyr Gln Met Pro Asp Gly
            260                 265                 270

Ser Val Ile Gly Asp Pro Ala Ser Val Glu Phe Thr Lys Leu Cys Ile
        275                 280                 285

Glu Leu Gly Trp Lys Pro Lys Tyr Gly Arg Phe Asp Val Val Pro Leu
    290                 295                 300

Ile Leu Gln Ala Asn Gly Gln Asp Pro Glu Ile Phe Glu Tyr Pro Pro
305                 310                 315                 320
```

```
Glu Ile Ile Leu Glu Val Pro Met Glu His Pro Lys Tyr Glu Trp Phe
                325                 330                 335
Lys Glu Leu Asp Leu Lys Trp Tyr Ala Leu Pro Ala Val Ala Asn Met
            340                 345                 350
Leu Leu Glu Val Gly Gly Leu Glu Phe Thr Ala Cys Pro Phe Asn Gly
        355                 360                 365
Trp Tyr Met Gly Thr Glu Ile Gly Val Arg Asp Phe Cys Asp Val Gln
    370                 375                 380
Arg Tyr Asn Ile Leu Lys Glu Val Gly Arg Met Gly Leu Glu Ser
385                 390                 395                 400
Asn Lys Leu Ala Ser Leu Trp Lys Asp Arg Ala Val Val Glu Ile Asn
            405                 410                 415
Val Ala Val Leu His Ser Phe Gln Lys Gln Asn Val Thr Ile Met Asp
        420                 425                 430
His His Ser Ala Ala Glu Ser Phe Met Lys Tyr Met Gln Asn Glu Tyr
    435                 440                 445
Arg Val Arg Gly Gly Cys Pro Ala Asp Trp Val Trp Ile Val Pro Pro
    450                 455                 460
Met Ser Gly Ser Ile Thr Pro Val Phe His Gln Glu Met Leu Asn Tyr
465                 470                 475                 480
Val Leu Thr Pro Phe Phe Tyr Tyr Gln Val Asp Ala Trp Lys Thr His
            485                 490                 495
Ile Trp His Asp Glu Thr Arg Arg Pro Lys Lys Arg Glu Ile Lys Leu
        500                 505                 510
Ser Ile Leu Ala Lys Ala Val Leu Leu Ala Ser Leu Leu Leu Gln Lys
    515                 520                 525
Thr Met Ala Ala Arg Pro Lys Val Thr Val Ile Tyr Ala Thr Glu Thr
    530                 535                 540
Gly Lys Ser Glu Thr Leu Ala Asn Ser Leu Cys Ser Leu Phe Ser Cys
545                 550                 555                 560
Ala Phe Asn Thr Lys Ile Leu Cys Met Asp Glu Tyr Asn Ile Ser Asp
            565                 570                 575
Leu Glu Lys Glu Thr Leu Leu Leu Val Val Thr Ser Thr Phe Gly Asn
        580                 585                 590
Gly Asp Ser Pro Asn Asn Gly Lys Thr Leu Lys Asn Ser Leu Leu Thr
    595                 600                 605
Leu Lys Leu Leu Arg Lys Asn Ile Arg Tyr Ala Val Phe Gly Leu Gly
    610                 615                 620
Ser Thr Met Tyr Pro Glu Phe Cys Ala Phe Ala His Ala Ile Asp Gln
625                 630                 635                 640
Lys Leu Ser Gln Leu Gly Ala Leu Gln Leu Thr Pro Val Gly Glu Gly
            645                 650                 655
Asp Glu Leu Asn Gly Gln Glu Glu Ala Phe Arg Thr Trp Ala Val Thr
        660                 665                 670
Ala Phe Lys Thr Ala Cys Asp Ile Phe Asp Ile Arg Gly Lys Asn Ser
    675                 680                 685
Ile Gln Leu Pro Glu Ile Tyr Thr Ser Asp Asp Ser Trp Asn Pro Lys
    690                 695                 700
Lys His Arg Ile Val Tyr Asp Ser Gln Thr Met Asp Leu Thr Lys Ala
705                 710                 715                 720
Leu Ser Asp Ile His Gly Lys Asn Val Ile Pro Met Lys Leu Lys Phe
            725                 730                 735
```

-continued

```
Arg Gln Asn Leu Gln Ser Leu Lys Ser Ser Arg Val Thr Ile Leu Val
            740                 745                 750
Lys Leu Ser Cys Glu Thr Asn Gln Glu Val His Tyr Leu Pro Gly Glu
        755                 760                 765
His Ile Gly Ile Ser Pro Gly Asn Gln Pro Glu Leu Val His Gly Leu
    770                 775                 780
Ile Ala Arg Val Lys Asp Ala Pro Pro Ala Asp Gln Thr Ile Arg Leu
785                 790                 795                 800
Glu Thr Cys Thr Glu Gly Gly Tyr Trp Ala Ser Glu Lys Lys Ile Pro
                805                 810                 815
Ala Cys Thr Leu Ser Gln Ala Leu Thr Tyr Leu Leu Asp Ile Thr Thr
            820                 825                 830
Pro Pro Thr Gln Gln Leu Leu Lys Lys Leu Ser Gln Leu Val Thr Ala
        835                 840                 845
Glu Gly Asp Lys Gln Arg Leu Glu Val Leu Cys His Ser Thr Glu Glu
    850                 855                 860
Tyr Asn Lys Trp Lys Phe Tyr Asn Arg Pro Asn Ile Leu Glu Val Leu
865                 870                 875                 880
Glu Glu Phe Pro Ser Ala Glu Val Ser Thr Ala Phe Leu Leu Thr Gln
                885                 890                 895
Leu Pro Leu Leu Lys Pro Arg Tyr Tyr Ser Val Ser Ser Ser Cys Asp
            900                 905                 910
Met Thr Pro Arg Glu Ile His Leu Thr Val Ala Val Val Asn Tyr Arg
        915                 920                 925
Thr Arg Asp Gly Gln Gly Pro Leu His His Gly Val Cys Ser Thr Trp
    930                 935                 940
Leu Asn Lys Ile Ala Leu Asn Glu Thr Val Pro Cys Phe Val Arg Ser
945                 950                 955                 960
Ala Asp Gly Phe Arg Leu Pro Lys Glu Pro Ala Lys Pro Cys Ile Leu
                965                 970                 975
Ile Gly Pro Gly Thr Gly Ile Ala Pro Phe Arg Ser Phe Trp Gln Gln
            980                 985                 990
Arg Leu Tyr Asp Leu Glu Lys Lys Gly Ile Lys Gly Gly Asp Met Ile
        995                 1000                1005
Leu Leu Phe Gly Cys Arg His Pro Asp Met Asp His Ile Tyr Lys Glu
    1010                1015                1020
Glu Val Glu Glu Met Lys Arg Lys Gly Val Leu Lys Glu Val Phe Thr
1025                1030                1035                1040
Ala Tyr Ser Arg Gln Pro Gly Gln Pro Lys Val Tyr Val Gln Asp Ile
                1045                1050                1055
Leu Gln Asn Glu Leu Glu Thr Lys Val Cys Asn Ile Leu His Lys Glu
            1060                1065                1070
Glu Gly His Leu Tyr Val Cys Gly Asp Val Arg Met Ala Arg Asp Val
        1075                1080                1085
Ala Gln Thr Leu Lys Arg Met Leu Val Lys Lys Leu Asn His Thr Glu
    1090                1095                1100
Gln Gln Ala Glu Glu Tyr Phe Phe Gln Leu Lys Ser Gln Lys Arg Tyr
1105                1110                1115                1120
His Glu Asp Ile Phe Gly Ala Val Phe Pro His Glu Val Lys Arg Ile
                1125                1130                1135

<210> SEQ ID NO 6
<211> LENGTH: 561
<212> TYPE: PRT
```

<213> ORGANISM: Mus musculus

<400> SEQUENCE: 6

```
Met Leu Phe Arg Ala Val Leu Leu Cys Ala Leu Gly Leu Ser Gln
 1               5                  10                  15

Ala Ala Asn Pro Cys Cys Ser Asn Pro Cys Gln Asn Arg Gly Glu Cys
            20                  25                  30

Met Ser Thr Gly Phe Asp Gln Tyr Lys Cys Asp Cys Thr Arg Thr Gly
        35                  40                  45

Phe Tyr Gly Glu Asn Cys Thr Thr Pro Glu Phe Leu Thr Arg Ile Lys
 50                  55                  60

Leu Leu Leu Lys Pro Thr Pro Asn Thr Val His Tyr Ile Leu Thr His
 65              70                  75                  80

Phe Lys Gly Val Trp Asn Ile Val Asn Asn Ile Pro Leu Leu Arg Ser
                    85                  90                  95

Leu Ile Met Lys Tyr Val Leu Thr Ser Arg Ser Tyr Leu Ile Asp Ser
                100                 105                 110

Pro Pro Thr Tyr Asn Val His Tyr Gly Tyr Lys Ser Trp Glu Ala Phe
            115                 120                 125

Ser Asn Leu Ser Tyr Tyr Thr Arg Ala Leu Pro Pro Val Ala Asp Asp
130                 135                 140

Cys Pro Thr Pro Met Gly Val Lys Gly Asn Lys Glu Leu Pro Asp Ser
145                 150                 155                 160

Lys Glu Val Leu Glu Lys Val Leu Leu Arg Arg Glu Phe Ile Pro Asp
                165                 170                 175

Pro Gln Gly Ser Asn Met Met Phe Ala Phe Phe Ala Gln His Phe Thr
            180                 185                 190

His Gln Phe Phe Lys Thr Asp His Lys Arg Gly Pro Gly Phe Thr Arg
        195                 200                 205

Gly Leu Gly His Gly Val Asp Leu Asn His Ile Tyr Gly Glu Thr Leu
    210                 215                 220

Asp Arg Gln His Lys Leu Arg Leu Phe Lys Asp Gly Lys Leu Lys Tyr
225                 230                 235                 240

Gln Val Ile Gly Gly Glu Val Tyr Pro Pro Thr Val Lys Asp Thr Gln
                245                 250                 255

Val Glu Met Ile Tyr Pro Pro His Ile Pro Glu Asn Leu Gln Phe Ala
            260                 265                 270

Val Gly Gln Glu Val Phe Gly Leu Val Pro Gly Leu Met Met Tyr Ala
        275                 280                 285

Thr Ile Trp Leu Arg Glu His Asn Arg Val Cys Asp Ile Leu Lys Phe
290                 295                 300

Asp Pro Glu Leu Leu Phe Asn Gln Gln Phe Gln Tyr Gln Asn Arg Ile
305                 310                 315                 320

Ala Ser Glu Phe Asn Thr Leu Tyr His Trp His Pro Leu Leu Pro Asp
                325                 330                 335

Thr Phe Asn Ile Glu Asp Gln Glu Tyr Ser Phe Lys Gln Phe Leu Tyr
            340                 345                 350

Asn Asn Ser Ile Leu Leu Glu His Gly Leu Thr Gln Phe Val Glu Ser
        355                 360                 365

Phe Thr Arg Gln Ile Ala Gly Arg Val Ala Gly Gly Arg Asn Val Pro
    370                 375                 380

Ile Ala Val Gln Ala Val Ala Lys Ala Ser Ile Asp Gln Ser Arg Glu
385                 390                 395                 400
```

-continued

```
Met Lys Tyr Gln Ser Leu Asn Glu Tyr Arg Lys Arg Phe Ser Leu Lys
                405                 410                 415
Pro Tyr Thr Ser Phe Glu Leu Thr Gly Glu Lys Glu Met Ala Ala
            420                 425                 430
Glu Leu Lys Ala Leu Tyr Ser Asp Ile Asp Val Met Glu Leu Tyr Pro
        435                 440                 445
Ala Leu Leu Val Glu Lys Pro Arg Pro Asp Ala Ile Phe Gly Glu Thr
450                 455                 460
Met Val Glu Leu Gly Ala Pro Phe Ser Leu Lys Gly Leu Met Gly Asn
465                 470                 475                 480
Pro Ile Cys Ser Pro Gln Tyr Trp Lys Pro Ser Thr Phe Gly Gly Glu
                485                 490                 495
Val Gly Phe Lys Ile Ile Asn Thr Ala Ser Ile Gln Ser Leu Ile Cys
            500                 505                 510
Asn Asn Val Lys Gly Cys Pro Phe Thr Ser Phe Asn Val Gln Asp Pro
        515                 520                 525
Gln Pro Thr Lys Thr Ala Thr Ile Asn Ala Ser Ala Ser His Ser Arg
    530                 535                 540
Leu Asp Asp Ile Asn Pro Thr Val Leu Ile Lys Arg Arg Ser Thr Glu
545                 550                 555                 560
Leu

<210> SEQ ID NO 7
<211> LENGTH: 604
<212> TYPE: PRT
<213> ORGANISM: Homo sapiens

<400> SEQUENCE: 7

Met Leu Ala Arg Ala Leu Leu Leu Cys Ala Val Leu Ala Leu Ser His
  1                 5                  10                  15
Thr Ala Asn Pro Cys Cys Ser His Pro Cys Gln Asn Arg Gly Val Cys
             20                  25                  30
Met Ser Val Gly Phe Asp Gln Tyr Lys Cys Asp Cys Thr Arg Thr Gly
         35                  40                  45
Phe Tyr Gly Glu Asn Cys Ser Thr Pro Glu Phe Leu Thr Arg Ile Lys
 50                  55                  60
Leu Phe Leu Lys Pro Thr Pro Asn Thr Val His Tyr Ile Leu Thr His
65                  70                  75                  80
Phe Lys Gly Phe Trp Asn Val Val Asn Asn Ile Pro Phe Leu Arg Asn
                 85                  90                  95
Ala Ile Met Ser Tyr Val Leu Thr Ser Arg Ser His Leu Ile Asp Ser
            100                 105                 110
Pro Pro Thr Tyr Asn Ala Asp Tyr Gly Tyr Lys Ser Trp Glu Ala Phe
        115                 120                 125
Ser Asn Leu Ser Tyr Tyr Thr Arg Ala Leu Pro Pro Val Pro Asp Asp
    130                 135                 140
Cys Pro Thr Pro Leu Gly Val Lys Gly Lys Lys Gln Leu Pro Asp Ser
145                 150                 155                 160
Asn Glu Ile Val Glu Lys Leu Leu Leu Arg Arg Lys Phe Ile Pro Asp
                165                 170                 175
Pro Gln Gly Ser Asn Met Met Phe Ala Phe Phe Ala Gln His Phe Thr
            180                 185                 190
His Gln Phe Phe Lys Thr Asp His Lys Arg Gly Pro Ala Phe Thr Asn
        195                 200                 205
```

```
Gly Leu Gly His Gly Val Asp Leu Asn His Ile Tyr Gly Glu Thr Leu
210                 215                 220

Ala Arg Gln Arg Lys Leu Arg Leu Phe Lys Asp Gly Lys Met Lys Tyr
225                 230                 235                 240

Gln Ile Ile Asp Gly Glu Met Tyr Pro Thr Val Lys Asp Thr Gln
                245                 250                 255

Ala Glu Met Ile Tyr Pro Pro Gln Val Pro Glu His Leu Arg Phe Ala
                260                 265                 270

Val Gly Gln Glu Val Phe Gly Leu Val Pro Gly Leu Met Met Tyr Ala
                275                 280                 285

Thr Ile Trp Leu Arg Glu His Asn Arg Val Cys Asp Val Leu Lys Gln
290                 295                 300

Glu His Pro Glu Trp Gly Asp Glu Gln Leu Phe Gln Thr Ser Arg Leu
305                 310                 315                 320

Ile Leu Ile Gly Glu Thr Ile Lys Ile Val Ile Glu Asp Tyr Val Gln
                325                 330                 335

His Leu Ser Gly Tyr His Phe Lys Leu Lys Phe Asp Pro Glu Leu Leu
                340                 345                 350

Phe Asn Lys Gln Phe Gln Tyr Gln Asn Arg Ile Ala Ala Glu Phe Asn
355                 360                 365

Thr Leu Tyr His Trp His Pro Leu Leu Pro Asp Thr Phe Gln Ile His
370                 375                 380

Asp Gln Lys Tyr Asn Tyr Gln Gln Phe Ile Tyr Asn Asn Ser Ile Leu
385                 390                 395                 400

Leu Glu His Gly Ile Thr Gln Phe Val Glu Ser Phe Thr Arg Gln Ile
                405                 410                 415

Ala Gly Arg Val Ala Gly Gly Arg Asn Val Pro Pro Ala Val Gln Lys
                420                 425                 430

Val Ser Gln Ala Ser Ile Asp Gln Ser Arg Gln Met Lys Tyr Gln Ser
                435                 440                 445

Phe Asn Glu Tyr Arg Lys Arg Phe Met Leu Lys Pro Tyr Glu Ser Phe
450                 455                 460

Glu Glu Leu Thr Gly Glu Lys Glu Met Ser Ala Glu Leu Glu Ala Leu
465                 470                 475                 480

Tyr Gly Asp Ile Asp Ala Val Glu Leu Tyr Pro Ala Leu Leu Val Glu
                485                 490                 495

Lys Pro Arg Pro Asp Ala Ile Phe Gly Glu Thr Met Val Glu Val Gly
                500                 505                 510

Ala Pro Phe Ser Leu Lys Gly Leu Met Gly Asn Val Ile Cys Ser Pro
                515                 520                 525

Ala Tyr Trp Lys Pro Ser Thr Phe Gly Gly Glu Val Gly Phe Gln Ile
530                 535                 540

Ile Asn Thr Ala Ser Ile Gln Ser Leu Ile Cys Asn Asn Val Lys Gly
545                 550                 555                 560

Cys Pro Phe Thr Ser Phe Ser Val Pro Asp Pro Glu Leu Ile Lys Thr
                565                 570                 575

Val Thr Ile Asn Ala Ser Ser Ser Arg Ser Gly Leu Asp Asp Ile Asn
                580                 585                 590

Pro Thr Val Leu Leu Lys Glu Arg Ser Thr Glu Leu
                595                 600
```

<210> SEQ ID NO 8
<211> LENGTH: 604
<212> TYPE: PRT

<213> ORGANISM: Rattus norvegicus

<400> SEQUENCE: 8

```
Met Leu Phe Arg Ala Val Leu Leu Cys Ala Cys Pro Gly Leu Ser His
1               5                   10                  15
Ala Ala Asn Pro Cys Cys Ser Asn Pro Cys Gln Asn Arg Gly Glu Cys
            20                  25                  30
Met Ser Ile Gly Phe Asp Gln Tyr Lys Cys Asp Cys Thr Arg Thr Gly
        35                  40                  45
Phe Tyr Gly Glu Asn Cys Thr Thr Pro Arg Phe Leu Thr Arg Ile Lys
    50                  55                  60
Leu Pro Leu Lys Pro Thr Pro Asn Thr Val His Tyr Ile Leu Thr His
65                  70                  75                  80
Phe Lys Gly Val Trp Asn Ile Val Asn Asn Ile Pro Phe Leu Arg Ile
                85                  90                  95
Gln Ser Met Arg Tyr Val Leu Thr Ser Arg Ser His Leu Ile Asp Ser
            100                 105                 110
Pro Pro Thr Tyr Asn Val His Tyr Gly Tyr Lys Ser Trp Glu Ala Phe
        115                 120                 125
Ser Asn Leu Ser Tyr Tyr Thr Arg Ala Leu Pro Pro Val Ala Asp Asp
    130                 135                 140
Cys Pro Thr Pro Met Gly Val Lys Gly Asn Lys Glu Leu Pro Asp Ser
145                 150                 155                 160
Lys Glu Val Leu Glu Lys Val Leu Leu Arg Arg Glu Phe Ile Pro Asp
                165                 170                 175
Pro Gln Gly Thr Asn Met Met Phe Ala Phe Phe Ala Gln His Phe Thr
            180                 185                 190
His Gln Phe Phe Lys Thr Asp Gln Lys Arg Gly Pro Gly Phe Thr Arg
        195                 200                 205
Gly Leu Gly His Gly Val Asp Leu Asn His Val Tyr Gly Glu Thr Leu
    210                 215                 220
Asp Arg Gln His Lys Leu Arg Leu Phe Gln Asp Gly Lys Leu Lys Tyr
225                 230                 235                 240
Gln Val Ile Gly Gly Glu Val Tyr Pro Pro Thr Val Lys Asp Thr Gln
                245                 250                 255
Val Asp Met Ile Tyr Pro Pro His Val Pro Glu His Leu Arg Phe Ala
            260                 265                 270
Val Gly Gln Glu Val Phe Gly Leu Val Pro Gly Leu Met Met Tyr Ala
        275                 280                 285
Thr Ile Trp Leu Arg Glu His Asn Arg Val Cys Asp Ile Leu Lys Gln
    290                 295                 300
Glu His Pro Glu Trp Asp Asp Glu Arg Leu Phe Gln Thr Ser Arg Leu
305                 310                 315                 320
Ile Leu Ile Gly Glu Thr Ile Lys Ile Val Ile Glu Asp Tyr Val Gln
                325                 330                 335
His Leu Arg Gly Tyr His Phe Gln Leu Lys Phe Asp Pro Asp Leu Leu
            340                 345                 350
Phe Asn Gln Gln Phe Gln Tyr Gln Asn Arg Ile Ala Ser Glu Phe Lys
        355                 360                 365
Thr Leu Tyr His Trp His Pro Leu Leu Pro Asp Thr Phe Asn Ile Glu
    370                 375                 380
Asp Gln Glu Tyr Thr Phe Lys Gln Phe Leu Tyr Asn Asn Ser Ile Leu
385                 390                 395                 400
```

```
Leu Glu His Gly Leu Ala His Phe Val Glu Ser Phe Thr Arg Gln Ile
                405                 410                 415

Ala Gly Arg Val Ala Gly Arg Asn Val Pro Ile Ala Val Gln Ala
            420                 425                 430

Val Ala Lys Ala Ser Ile Asp Gln Ser Arg Glu Met Lys Tyr Gln Ser
                435                 440                 445

Leu Asn Glu Tyr Arg Lys Arg Phe Ser Leu Lys Pro Tyr Thr Ser Phe
450                 455                 460

Glu Glu Leu Thr Gly Glu Lys Glu Met Ala Ala Glu Leu Lys Ala Leu
465                 470                 475                 480

Tyr His Asp Ile Asp Ala Met Glu Leu Tyr Pro Ala Leu Leu Val Glu
                485                 490                 495

Lys Pro Arg Pro Asp Ala Ile Phe Gly Glu Thr Met Val Glu Leu Gly
                500                 505                 510

Ala Pro Phe Ser Leu Lys Gly Leu Met Gly Asn Pro Ile Cys Ser Pro
                515                 520                 525

Gln Tyr Trp Lys Pro Ser Thr Phe Gly Gly Glu Val Gly Phe Arg Ile
530                 535                 540

Ile Asn Thr Ala Ser Ile Gln Ser Leu Ile Cys Asn Asn Val Lys Gly
545                 550                 555                 560

Cys Pro Phe Ala Ser Phe Asn Val Gln Asp Pro Gln Ala Thr Lys Thr
                565                 570                 575

Ala Thr Ile Asn Ala Ser Ala Ser His Ser Arg Leu Asp Asp Ile Asn
                580                 585                 590

Pro Thr Val Leu Ile Lys Arg Ser Thr Glu Leu
                595                 600

<210> SEQ ID NO 9
<211> LENGTH: 603
<212> TYPE: PRT
<213> ORGANISM: Sheep

<400> SEQUENCE: 9

Met Leu Ala Arg Ala Leu Leu Cys Ala Val Val Cys Gly Ala
 1               5                  10                  15

Ala Asn Pro Cys Cys Ser His Pro Cys Gln Asn Arg Gly Val Cys Met
                20                  25                  30

Ser Val Gly Phe Asp Gln Tyr Lys Cys Asp Cys Thr Arg Thr Gly Phe
                35                  40                  45

Tyr Gly Glu Asn Cys Thr Thr Pro Glu Phe Leu Thr Arg Ile Lys Leu
50                  55                  60

Leu Leu Lys Pro Thr Pro Asp Thr Val His Tyr Ile Leu Thr His Phe
65                  70                  75                  80

Lys Gly Val Trp Asn Ile Val Asn Lys Ile Ser Phe Leu Arg Asn Met
                85                  90                  95

Ile Met Arg Tyr Val Leu Thr Ser Arg Ser His Leu Ile Glu Ser Pro
                100                 105                 110

Pro Thr Tyr Asn Val His Tyr Ser Tyr Lys Ser Trp Glu Ala Phe Ser
                115                 120                 125

Asn Leu Ser Tyr Tyr Thr Arg Ala Leu Pro Pro Val Pro Asp Asp Cys
130                 135                 140

Pro Thr Pro Met Gly Val Lys Gly Arg Lys Glu Leu Pro Asp Ser Lys
145                 150                 155                 160

Glu Val Val Lys Lys Val Leu Leu Arg Arg Lys Phe Ile Pro Asp Pro
                165                 170                 175
```

```
Gln Gly Thr Asn Leu Met Phe Ala Phe Phe Ala Gln His Phe Thr His
            180                 185                 190
Gln Phe Phe Lys Thr Asp Ile Glu Arg Gly Pro Ala Phe Thr Lys Gly
            195                 200                 205
Lys Asn His Gly Val Asp Leu Ser His Val Tyr Gly Glu Ser Leu Glu
            210                 215                 220
Arg Gln His Asn Arg Arg Leu Phe Lys Asp Gly Lys Met Lys Tyr Gln
225                 230                 235                 240
Met Ile Asn Gly Glu Met Tyr Pro Pro Thr Val Lys Asp Thr Gln Val
                    245                 250                 255
Glu Met Ile Tyr Pro Pro His Ile Pro Glu His Leu Lys Phe Ala Val
                260                 265                 270
Gly Gln Glu Val Phe Gly Leu Pro Gly Leu Met Met Tyr Ala Thr
            275                 280                 285
Ile Trp Leu Arg Glu His Asn Arg Val Cys Asp Val Leu Lys Gln Glu
            290                 295                 300
His Pro Glu Trp Gly Asp Glu Gln Leu Phe Gln Thr Ser Arg Leu Ile
305                 310                 315                 320
Leu Ile Gly Glu Thr Ile Lys Ile Val Ile Glu Asp Tyr Val Gln His
                325                 330                 335
Leu Ser Gly Tyr His Phe Lys Leu Lys Phe Asp Pro Glu Leu Leu Phe
                340                 345                 350
Asn Gln Gln Phe Gln Tyr Gln Asn Arg Ile Ala Ala Glu Phe Asn Thr
            355                 360                 365
Leu Tyr His Trp His Pro Leu Leu Pro Asp Val Phe Gln Ile Asp Gly
            370                 375                 380
Gln Glu Tyr Asn Tyr Gln Gln Phe Ile Tyr Asn Asn Ser Val Leu Leu
385                 390                 395                 400
Glu His Gly Val Thr Gln Phe Val Glu Ser Phe Thr Arg Gln Ile Ala
                405                 410                 415
Gly Arg Val Ala Gly Arg Arg Asn Leu Pro Ala Ala Val Glu Lys Val
            420                 425                 430
Ser Lys Ala Ser Leu Asp Gln Ser Arg Glu Met Lys Tyr Gln Ser Phe
            435                 440                 445
Asn Glu Tyr Arg Lys Arg Phe Leu Leu Lys Pro Tyr Glu Ser Phe Glu
            450                 455                 460
Glu Leu Thr Gly Glu Lys Glu Met Ala Ala Glu Leu Glu Ala Leu Tyr
465                 470                 475                 480
Gly Asp Ile Asp Ala Met Glu Leu Tyr Pro Ala Leu Leu Val Glu Lys
                485                 490                 495
Pro Ala Pro Asp Ala Ile Phe Gly Glu Thr Met Val Glu Ala Gly Ala
                500                 505                 510
Pro Phe Ser Leu Lys Gly Leu Met Gly Asn Pro Ile Cys Ser Pro Glu
            515                 520                 525
Tyr Trp Lys Pro Ser Thr Phe Gly Gly Glu Val Gly Phe Lys Ile Ile
            530                 535                 540
Asn Thr Ala Ser Ile Gln Ser Leu Ile Cys Ser Asn Val Lys Gly Cys
545                 550                 555                 560
Pro Phe Thr Ser Phe Ser Val Gln Asp Ala His Leu Thr Lys Thr Val
                565                 570                 575
Thr Ile Asn Ala Ser Ser Ser His Ser Gly Leu Asp Asp Ile Asn Pro
                580                 585                 590
```

```
Thr Val Leu Leu Lys Glu Arg Ser Thr Glu Leu
        595                 600
```

<210> SEQ ID NO 10
<211> LENGTH: 604
<212> TYPE: PRT
<213> ORGANISM: Bos bovus

<400> SEQUENCE: 10

```
Met Leu Ala Arg Ala Leu Leu Cys Ala Val Ala Leu Ser Gly
 1               5                  10                  15

Ala Ala Asn Pro Cys Cys Ser His Pro Cys Gln Asn Arg Gly Val Cys
            20                  25                  30

Met Ser Val Gly Phe Asp Gln Tyr Lys Cys Asp Cys Thr Arg Thr Gly
        35                  40                  45

Phe Tyr Gly Glu Asn Cys Thr Thr Pro Glu Phe Leu Thr Arg Ile Lys
    50                  55                  60

Leu Leu Leu Lys Pro Thr Pro Asn Thr Val His Tyr Ile Leu Thr His
65                  70                  75                  80

Phe Lys Gly Val Trp Asn Ile Val Asn Lys Ile Ser Phe Leu Arg Asn
                85                  90                  95

Met Ile Met Arg Tyr Val Leu Thr Ser Arg Ser His Leu Ile Glu Ser
            100                 105                 110

Pro Pro Thr Tyr Asn Val His Tyr Ser Tyr Lys Ser Trp Glu Ala Phe
        115                 120                 125

Ser Asn Leu Ser Tyr Tyr Thr Arg Ala Leu Pro Pro Val Pro Asp Asp
    130                 135                 140

Cys Pro Thr Pro Met Gly Val Lys Gly Arg Lys Glu Leu Pro Asp Ser
145                 150                 155                 160

Lys Glu Val Val Lys Lys Val Leu Leu Arg Arg Lys Phe Ile Pro Asp
                165                 170                 175

Pro Gln Gly Thr Asn Leu Met Phe Ala Phe Phe Ala Gln His Phe Thr
            180                 185                 190

His Gln Phe Phe Lys Thr Asp Phe Glu Arg Gly Pro Ala Phe Thr Lys
        195                 200                 205

Gly Lys Asn His Gly Val Asp Leu Ser His Ile Tyr Gly Glu Ser Leu
    210                 215                 220

Glu Arg Gln His Lys Leu Arg Leu Phe Lys Asp Gly Lys Met Lys Tyr
225                 230                 235                 240

Gln Met Ile Asn Gly Glu Met Tyr Pro Pro Thr Val Lys Asp Thr Gln
                245                 250                 255

Val Glu Met Ile Tyr Pro Pro His Val Pro Glu His Leu Lys Phe Ala
            260                 265                 270

Val Gly Gln Glu Val Phe Gly Leu Val Pro Gly Leu Met Met Tyr Ala
        275                 280                 285

Thr Ile Trp Leu Arg Glu His Asn Arg Val Cys Asp Val Leu Lys Gln
    290                 295                 300

Glu His Pro Glu Trp Gly Asp Glu Gln Leu Phe Gln Thr Ser Arg Leu
305                 310                 315                 320

Ile Leu Ile Gly Glu Thr Ile Lys Ile Val Ile Glu Asp Tyr Val Gln
                325                 330                 335

His Leu Ser Gly Tyr His Phe Lys Leu Lys Phe Asp Pro Glu Leu Leu
            340                 345                 350

Phe Asn Gln Gln Phe Gln Tyr Gln Asn Arg Ile Ala Ala Glu Phe Asn
        355                 360                 365
```

```
Thr Leu Tyr His Trp His Pro Leu Pro Asp Val Phe Gln Ile Asp
    370                 375                 380

Gly Gln Glu Tyr Asn Tyr Gln Gln Phe Ile Tyr Asn Asn Ser Val Leu
385                 390                 395                 400

Leu Glu His Gly Leu Thr Gln Phe Val Glu Ser Phe Thr Arg Gln Arg
                405                 410                 415

Ala Gly Arg Val Ala Gly Arg Asn Leu Pro Val Ala Val Glu Lys
            420                 425                 430

Val Ser Lys Ala Ser Ile Asp Gln Ser Arg Glu Met Lys Tyr Gln Ser
            435                 440                 445

Phe Asn Glu Tyr Arg Lys Arg Phe Leu Val Lys Pro Tyr Glu Ser Phe
    450                 455                 460

Glu Glu Leu Thr Gly Glu Lys Glu Met Ala Ala Glu Leu Glu Ala Leu
465                 470                 475                 480

Tyr Gly Asp Ile Asp Ala Met Glu Phe Tyr Pro Ala Leu Leu Val Glu
                485                 490                 495

Lys Pro Arg Pro Asp Ala Ile Phe Gly Glu Thr Met Val Glu Ala Gly
            500                 505                 510

Ala Pro Phe Ser Leu Lys Gly Leu Met Gly Asn Pro Ile Cys Ser Pro
            515                 520                 525

Glu Tyr Trp Lys Pro Ser Thr Phe Gly Gly Glu Val Gly Phe Lys Ile
    530                 535                 540

Ile Asn Thr Ala Ser Ile Gln Ser Leu Ile Cys Ser Asn Val Lys Gly
545                 550                 555                 560

Cys Pro Phe Thr Ser Phe Ser Val Gln Asp Thr His Leu Thr Lys Thr
                565                 570                 575

Val Thr Ile Asn Ala Ser Ser His Ser Gly Leu Asp Asp Ile Asn
            580                 585                 590

Pro Thr Val Leu Leu Lys Glu Arg Ser Thr Glu Leu
            595                 600

<210> SEQ ID NO 11
<211> LENGTH: 604
<212> TYPE: PRT
<213> ORGANISM: Horse

<400> SEQUENCE: 11

Met Leu Ala Arg Ala Leu Leu Cys Val Ala Leu Ala Leu Gly His
 1               5                  10                  15

Ala Ala Asn Pro Cys Cys Ser Asn Pro Cys Gln Asn Arg Gly Val Cys
                20                  25                  30

Met Ser Val Gly Phe Asp Gln Tyr Gln Cys Asp Cys Thr Arg Thr Gly
            35                  40                  45

Phe Tyr Gly Glu Asn Cys Ser Thr Pro Glu Phe Leu Thr Arg Ile Lys
    50                  55                  60

Leu Phe Leu Lys Pro Thr Pro Asn Thr Val His Tyr Ile Leu Thr His
65                  70                  75                  80

Phe Lys Gly Val Trp Asn Ile Val Asn Ser Phe Pro Phe Leu Arg Asn
                85                  90                  95

Ala Val Met Lys Tyr Val Leu Val Ser Arg Ser His Leu Ile Glu Ser
            100                 105                 110

Pro Pro Thr Tyr Asn Ala Gln Tyr Gly Tyr Lys Ser Trp Glu Ser Phe
        115                 120                 125

Ser Asn Leu Ser Tyr Tyr Thr Arg Ala Leu Pro Pro Val Ala Asp Gly
```

-continued

```
            130                 135                 140
Cys Pro Thr Pro Met Gly Val Lys Gly Lys Glu Leu Pro Asp Ser
145                 150                 155                 160
Lys Glu Ile Val Glu Lys Phe Leu Leu Arg Arg Lys Phe Ile Pro Asp
                165                 170                 175
Pro Gln Gly Thr Asn Met Met Phe Ala Phe Ala Gln His Phe Thr
                180                 185                 190
His Gln Phe Phe Lys Thr Asp Pro Lys Arg Gly Pro Ala Phe Thr Lys
                195                 200                 205
Gly Leu Gly His Gly Val Asp Leu Ser His Ile Tyr Gly Glu Thr Leu
210                 215                 220
Asp Arg Gln His Lys Leu Arg Leu Phe Lys Asp Gly Lys Met Lys Tyr
225                 230                 235                 240
Gln Ile Ile Asn Gly Glu Val Tyr Pro Pro Thr Val Lys Asp Thr Gln
                245                 250                 255
Val Glu Met Ile Tyr Pro Pro His Ile Pro Glu His Leu Arg Phe Ala
                260                 265                 270
Val Gly Gln Glu Val Phe Gly Leu Val Pro Gly Leu Met Met Tyr Ala
                275                 280                 285
Thr Ile Trp Leu Arg Glu His Asn Arg Val Cys Asp Val Leu Lys Gln
                290                 295                 300
Glu His Pro Glu Trp Asp Asp Glu Arg Leu Phe Gln Thr Ser Arg Leu
305                 310                 315                 320
Ile Leu Ile Gly Glu Thr Ile Lys Ile Val Ile Glu Asp Tyr Val Gln
                325                 330                 335
His Leu Ser Gly Tyr His Phe Lys Leu Lys Phe Asp Pro Glu Leu Leu
                340                 345                 350
Phe Asn Gln Gln Phe Gln Tyr Gln Asn Arg Ile Ala Ala Glu Phe Asn
                355                 360                 365
Thr Leu Tyr His Trp His Pro Leu Leu Pro Asp Thr Phe Gln Ile Asp
                370                 375                 380
Asp Gln Glu Tyr Asn Phe Gln Gln Phe Leu Tyr Asn Asn Ser Ile Leu
385                 390                 395                 400
Leu Glu His Gly Leu Thr Gln Phe Val Glu Ser Phe Ser Arg Gln Ile
                405                 410                 415
Ala Gly Arg Val Ala Gly Gly Arg Asn Val Pro Ala Ala Gln Lys
                420                 425                 430
Ile Ala Lys Ala Ser Ile Asp Gln Ser Arg Glu Met Lys Tyr Gln Ser
                435                 440                 445
Leu Asn Glu Tyr Arg Lys Arg Phe Arg Leu Thr Pro Tyr Lys Ser Phe
450                 455                 460
Glu Glu Leu Thr Gly Glu Lys Glu Met Ala Ala Glu Leu Glu Ala Leu
465                 470                 475                 480
Tyr Gly Asp Ile Asp Ala Met Glu Leu Tyr Pro Ala Leu Leu Val Glu
                485                 490                 495
Lys Pro Arg Pro Asp Ala Ile Phe Gly Glu Thr Met Val Glu Leu Gly
                500                 505                 510
Ala Pro Phe Ser Leu Lys Gly Leu Leu Gly Asn Pro Ile Cys Ser Pro
                515                 520                 525
Asp Tyr Trp Lys Pro Ser Thr Phe Gly Gly Glu Val Gly Phe Lys Ile
                530                 535                 540
Ile Asn Thr Ala Ser Ile Gln Ser Leu Ile Cys Asn Asn Val Lys Gly
545                 550                 555                 560
```

-continued

```
Cys Pro Phe Thr Ala Phe Ser Val Gln Asp Pro Gln Leu Ser Lys Ala
                565                 570                 575
Val Thr Ile Asn Ala Ser Ala Ser His Ser Gly Leu Asp Asp Val Asn
            580                 585                 590
Pro Thr Val Leu Leu Lys Glu Arg Ser Thr Glu Leu
        595                 600

<210> SEQ ID NO 12
<211> LENGTH: 604
<212> TYPE: PRT
<213> ORGANISM: Rabbit

<400> SEQUENCE: 12

Met Leu Ala Arg Ala Leu Leu Cys Ala Val Ala Leu Ser His
 1               5                  10                  15
Ala Ala Asn Pro Cys Cys Ser Asn Pro Cys Gln Asn Arg Gly Val Cys
            20                  25                  30
Met Thr Met Gly Phe Asp Gln Tyr Lys Cys Asp Cys Thr Arg Thr Gly
        35                  40                  45
Phe Tyr Gly Glu Asn Cys Ser Thr Pro Glu Phe Leu Thr Arg Ile Lys
 50                  55                  60
Leu Leu Leu Lys Pro Thr Pro Asp Thr Val His Tyr Ile Leu Thr His
65                  70                  75                  80
Phe Lys Gly Val Trp Asn Ile Val Asn Ser Ile Pro Phe Leu Arg Asn
                85                  90                  95
Ser Ile Met Lys Tyr Val Leu Thr Ser Arg Ser His Met Ile Asp Ser
            100                 105                 110
Pro Pro Thr Tyr Asn Val His Tyr Asn Tyr Lys Ser Trp Glu Ala Phe
        115                 120                 125
Ser Asn Leu Ser Tyr Tyr Thr Arg Ala Leu Pro Pro Val Ala Asp Asp
130                 135                 140
Cys Pro Thr Pro Met Gly Val Lys Gly Lys Lys Glu Leu Pro Asp Ser
145                 150                 155                 160
Lys Asp Val Val Glu Lys Leu Leu Leu Arg Arg Lys Phe Ile Pro Asp
                165                 170                 175
Pro Gln Gly Thr Asn Met Met Phe Ala Phe Phe Ala Gln His Phe Thr
            180                 185                 190
His Gln Phe Phe Lys Thr Asp Leu Lys Arg Gly Pro Ala Phe Thr Lys
        195                 200                 205
Gly Leu Gly His Gly Val Asp Leu Asn His Ile Tyr Gly Glu Thr Leu
210                 215                 220
Asp Arg Gln His Lys Leu Arg Leu Phe Lys Asp Gly Lys Met Lys Tyr
225                 230                 235                 240
Gln Val Ile Asp Gly Glu Val Tyr Pro Pro Thr Val Lys Asp Thr Gln
                245                 250                 255
Val Glu Met Ile Tyr Pro Pro His Ile Pro Ala His Leu Gln Phe Ala
            260                 265                 270
Val Gly Gln Glu Val Phe Gly Leu Val Pro Gly Leu Met Met Tyr Ala
        275                 280                 285
Thr Ile Trp Leu Arg Glu His Asn Arg Val Cys Asp Val Leu Lys Gln
290                 295                 300
Glu His Pro Glu Trp Asp Asp Glu Gln Leu Phe Gln Thr Ser Arg Leu
305                 310                 315                 320
Ile Leu Ile Gly Glu Thr Ile Lys Ile Val Ile Glu Asp Tyr Val Gln
```

```
                    325                 330                 335
His Leu Ser Gly Tyr His Phe Lys Leu Lys Phe Asp Pro Glu Leu Leu
                340                 345                 350

Phe Asn Gln Gln Phe Gln Tyr Gln Asn Arg Ile Ala Ala Glu Phe Asn
            355                 360                 365

Thr Leu Tyr His Trp His Pro Leu Leu Pro Asp Thr Phe Gln Ile Asp
        370                 375                 380

Asp Gln Gln Tyr Asn Tyr Gln Gln Phe Leu Tyr Asn Asn Ser Ile Leu
385                 390                 395                 400

Leu Glu His Gly Leu Thr Gln Phe Val Glu Ser Phe Thr Arg Gln Ile
                405                 410                 415

Ala Gly Arg Val Ala Gly Arg Asn Val Pro Pro Ala Val Gln Lys
                420                 425                 430

Val Ala Lys Ala Ser Ile Asp Gln Ser Arg Gln Met Lys Tyr Gln Ser
            435                 440                 445

Leu Asn Glu Tyr Arg Lys Arg Phe Leu Leu Lys Pro Tyr Glu Ser Phe
        450                 455                 460

Glu Glu Leu Thr Gly Glu Lys Glu Met Ala Ala Glu Leu Glu Ala Leu
465                 470                 475                 480

Tyr Gly Asp Ile Asp Ala Val Glu Leu Tyr Pro Ala Leu Leu Val Glu
                485                 490                 495

Arg Pro Arg Pro Asp Ala Ile Phe Gly Glu Ser Met Val Glu Met Gly
                500                 505                 510

Ala Pro Phe Ser Leu Lys Gly Leu Met Gly Asn Pro Ile Cys Ser Pro
            515                 520                 525

Asn Tyr Trp Lys Pro Ser Thr Phe Gly Gly Glu Val Gly Phe Lys Ile
        530                 535                 540

Val Asn Thr Ala Ser Ile Gln Ser Leu Ile Cys Asn Asn Val Lys Gly
545                 550                 555                 560

Cys Pro Phe Thr Ser Phe Asn Val Pro Asp Pro Gln Leu Thr Lys Thr
                565                 570                 575

Val Thr Ile Asn Ala Ser Ala Ser His Ser Arg Leu Glu Asp Ile Asn
            580                 585                 590

Pro Thr Val Leu Leu Lys Gly Arg Ser Thr Glu Leu
        595                 600

<210> SEQ ID NO 13
<211> LENGTH: 604
<212> TYPE: PRT
<213> ORGANISM: Canis familiaris

<400> SEQUENCE: 13

Met Leu Ala Arg Ala Leu Val Leu Cys Ala Ala Leu Ala Val Val Arg
1               5                   10                  15

Ala Ala Asn Pro Cys Cys Ser His Pro Cys Gln Asn Gln Gly Ile Cys
                20                  25                  30

Met Ser Thr Gly Phe Asp Gln Tyr Lys Cys Asp Cys Thr Arg Thr Gly
            35                  40                  45

Phe Tyr Gly Glu Asn Cys Ser Thr Pro Glu Phe Leu Thr Arg Ile Lys
        50                  55                  60

Leu Tyr Leu Lys Pro Thr Pro Asn Thr Val His Tyr Ile Leu Thr His
65                  70                  75                  80

Phe Lys Gly Val Trp Asn Ile Val Asn Asn Ile Pro Phe Leu Arg Asn
                85                  90                  95
```

```
Thr Ile Met Lys Tyr Val Leu Thr Ser Arg Ser His Leu Ile Glu Ser
            100                 105                 110

Pro Pro Thr Tyr Asn Val Asn Tyr Gly Tyr Lys Ser Trp Glu Ala Phe
            115                 120                 125

Ser Asn Leu Ser Tyr Tyr Thr Arg Ala Leu Pro Pro Val Pro Asp Asp
            130                 135                 140

Cys Pro Thr Pro Met Gly Val Lys Gly Lys Lys Glu Leu Pro Asp Ser
145                 150                 155                 160

Lys Glu Ile Val Glu Lys Phe Leu Leu Arg Arg Lys Phe Ile Pro Asp
            165                 170                 175

Pro Gln Gly Thr Asn Met Met Phe Ala Phe Phe Ala Gln His Phe Thr
            180                 185                 190

His Gln Phe Phe Lys Thr Asp His Lys Arg Gly Pro Ala Phe Thr Lys
            195                 200                 205

Gly Leu Gly His Gly Val Asp Leu Asn His Val Tyr Gly Glu Thr Leu
            210                 215                 220

Asp Arg Gln His Lys Leu Arg Leu Phe Lys Asp Gly Lys Met Lys Tyr
225                 230                 235                 240

Gln Val Ile Asp Gly Glu Val Tyr Pro Pro Thr Val Lys Asp Thr Gln
            245                 250                 255

Val Glu Met Ile Tyr Pro Pro His Val Pro Glu His Leu Gln Phe Ala
            260                 265                 270

Val Gly Gln Glu Val Phe Gly Leu Val Pro Gly Leu Met Met Tyr Ala
            275                 280                 285

Thr Ile Trp Leu Arg Glu His Asn Arg Val Cys Asp Val Leu Lys Gln
            290                 295                 300

Glu His Pro Glu Trp Asp Asp Glu Arg Leu Phe Gln Thr Ser Arg Leu
305                 310                 315                 320

Ile Leu Ile Gly Glu Thr Ile Lys Ile Val Ile Glu Asp Tyr Val Gln
            325                 330                 335

His Leu Ser Gly Tyr His Phe Lys Leu Lys Phe Asp Pro Glu Leu Leu
            340                 345                 350

Phe Asn Gln Gln Phe Gln Tyr Gln Asn Arg Ile Ala Ala Glu Phe Asn
            355                 360                 365

Thr Leu Tyr His Trp His Pro Leu Leu Pro Asp Thr Leu Gln Ile Asp
            370                 375                 380

Asp Gln Glu Tyr Asn Phe Gln Gln Phe Ile Tyr Asn Asn Ser Ile Leu
385                 390                 395                 400

Leu Glu His Gly Leu Thr Gln Phe Val Glu Ser Phe Ser Arg Gln Ile
            405                 410                 415

Ala Gly Arg Val Ala Gly Gly Arg Asn Val Pro Ala Ala Val Gln Gln
            420                 425                 430

Val Ala Lys Ala Ser Ile Asp Gln Ser Arg Gln Met Lys Tyr Gln Ser
            435                 440                 445

Leu Asn Glu Tyr Arg Lys Arg Phe Arg Leu Lys Pro Tyr Thr Ser Phe
            450                 455                 460

Glu Glu Leu Thr Gly Glu Lys Glu Met Ala Ala Gly Leu Glu Ala Leu
465                 470                 475                 480

Tyr Gly Asp Ile Asp Ala Met Glu Leu Tyr Pro Ala Leu Leu Val Glu
            485                 490                 495

Lys Pro Arg Pro Asp Ala Ile Phe Gly Glu Thr Met Val Glu Met Gly
            500                 505                 510

Ala Pro Phe Ser Leu Lys Gly Leu Met Gly Asn Pro Ile Cys Ser Pro
```

```
                515                 520                 525
Asp Tyr Trp Lys Pro Ser Thr Phe Gly Gly Glu Val Gly Phe Lys Ile
            530                 535                 540

Ile Asn Thr Ala Ser Ile Gln Ser Leu Ile Cys Asn Asn Val Lys Gly
545                 550                 555                 560

Cys Pro Phe Thr Ala Phe Ser Val Gln Asp Gly Gln Leu Thr Lys Thr
                565                 570                 575

Val Thr Ile Asn Ala Ser Ser Ser His Ser Gly Leu Asp Asp Ile Asn
            580                 585                 590

Pro Thr Val Leu Leu Lys Glu Arg Ser Thr Glu Leu
                595                 600

<210> SEQ ID NO 14
<211> LENGTH: 604
<212> TYPE: PRT
<213> ORGANISM: Sus scrofa

<400> SEQUENCE: 14

Met Leu Ala Arg Ala Leu Leu Cys Ala Ala Val Ser Leu Cys Thr
 1               5                  10                  15

Ala Ala Lys Pro Cys Cys Ser Asn Pro Cys Gln Asn Arg Gly Ile Cys
            20                  25                  30

Met Ser Val Gly Phe Asp His Tyr Lys Cys Asp Cys Thr Arg Thr Gly
        35                  40                  45

Phe Tyr Gly Glu Asn Cys Thr Thr Pro Glu Phe Leu Thr Arg Ile Lys
    50                  55                  60

Leu Phe Leu Lys Pro Thr Pro Asn Thr Val His Tyr Ile Leu Thr His
65                  70                  75                  80

Phe Lys Gly Val Trp Asn Ile Val Asn Asn Ile Pro Phe Leu Arg Asn
                85                  90                  95

Ala Ile Met Lys Tyr Val Leu Ile Ser Arg Ser His Leu Ile Asp Ser
            100                 105                 110

Pro Pro Thr Tyr Asn Met His Tyr Gly Tyr Lys Ser Trp Glu Ala Phe
        115                 120                 125

Ser Asn Leu Ser Tyr Tyr Thr Arg Ala Leu Pro Pro Val Pro Asp Asp
    130                 135                 140

Cys Pro Thr Pro Met Gly Val Lys Gly Arg Lys Glu Leu Pro Asp Ser
145                 150                 155                 160

Lys Glu Val Val Glu Lys Leu Leu Leu Arg Arg Lys Phe Ile Pro Asp
                165                 170                 175

Pro Gln Gly Thr Asn Met Met Phe Ala Phe Phe Ala Gln His Phe Thr
            180                 185                 190

His Gln Phe Phe Lys Thr Asp Gln Lys Arg Gly Pro Ala Phe Thr Lys
        195                 200                 205

Gly Gln Gly His Gly Val Asp Leu Ser His Val Tyr Gly Glu Ser Leu
    210                 215                 220

Glu Arg Gln His Lys Leu Arg Leu Phe Lys Asp Gly Lys Met Lys Tyr
225                 230                 235                 240

Gln Ile Ile Asp Gly Glu Met Tyr Pro Pro Thr Ala Lys Asp Thr Gln
                245                 250                 255

Val Glu Met Ile Tyr Pro Pro His Thr Pro Glu His Leu Arg Phe Ala
            260                 265                 270

Val Gly His Glu Val Phe Gly Leu Val Pro Gly Leu Met Met Tyr Ala
        275                 280                 285
```

-continued

```
Thr Ile Trp Leu Arg Glu His Asn Arg Val Cys Asp Val Leu Lys Gln
    290                 295                 300

Glu His Pro Glu Trp Asp Asp Glu Arg Leu Phe Gln Thr Ser Arg Leu
305                 310                 315                 320

Ile Leu Ile Gly Glu Thr Ile Lys Ile Val Ile Glu Asp Tyr Val Gln
                325                 330                 335

His Leu Ser Gly Tyr His Phe Lys Leu Lys Phe Asp Pro Glu Leu Leu
                340                 345                 350

Phe Asn Gln Gln Phe Gln Tyr Gln Asn Arg Ile Ala Ala Glu Phe Asn
                    355                 360                 365

Thr Leu Tyr His Trp His Pro Leu Leu Pro Asp Ala Phe Gln Ile Asp
    370                 375                 380

Gly His Glu Tyr Asn Tyr Gln Gln Phe Leu Tyr Asn Asn Ser Ile Leu
385                 390                 395                 400

Leu Glu His Gly Ile Thr Gln Phe Val Glu Ser Phe Ser Arg Gln Ile
                405                 410                 415

Ala Gly Arg Val Ala Gly Gly Arg Asn Leu Pro Ala Ala Val Gln Lys
                420                 425                 430

Val Ser Lys Ala Ser Ile Asp Gln Ser Arg Glu Met Arg Tyr Gln Ser
            435                 440                 445

Phe Asn Glu Tyr Arg Lys Arg Phe Leu Leu Lys Pro Tyr Arg Ser Phe
    450                 455                 460

Glu Glu Leu Thr Gly Glu Lys Glu Met Ala Ala Glu Leu Glu Ala Leu
465                 470                 475                 480

Tyr Gly Asp Ile Asp Ala Met Glu Leu Tyr Pro Ala Leu Leu Val Glu
                485                 490                 495

Lys Pro Arg Pro Asp Ala Ile Phe Gly Glu Thr Met Val Glu Ala Gly
                500                 505                 510

Ala Pro Phe Ser Leu Lys Gly Leu Met Gly Asn Pro Ile Cys Ser Pro
            515                 520                 525

Glu Tyr Trp Lys Pro Ser Thr Phe Gly Gly Glu Val Gly Phe Lys Ile
    530                 535                 540

Ile Asn Thr Ala Ser Ile Gln Ser Leu Ile Cys Asn Asn Val Lys Gly
545                 550                 555                 560

Cys Pro Phe Thr Ser Phe Ser Val Gln Asp Pro Gln Leu Ala Lys Thr
                565                 570                 575

Val Thr Ile Asn Ala Ser Ser Ser His Ser Gly Leu Asp Asp Ile Asn
                580                 585                 590

Pro Thr Val Leu Leu Lys Glu Arg Ser Thr Glu Leu
        595                 600
```